US012574017B2

(12) United States Patent
Pattipaka et al.

(10) Patent No.: US 12,574,017 B2
(45) Date of Patent: Mar. 10, 2026

(54) METHODS AND APPARATUS TO CORRECT NON-LINEARITY IN TRANSMITTERS

(71) Applicant: Texas Instruments Incorporated, Dallas, TX (US)

(72) Inventors: Ravikumar Pattipaka, Bangalore (IN); Savyan Kanisserry, Bangalore (IN); Raja Sekhar, Bangalore (IN); Sandeep Oswal, Bangalore (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 18/620,293

(22) Filed: Mar. 28, 2024

(65) Prior Publication Data

US 2025/0309867 A1 Oct. 2, 2025

(51) Int. Cl.
H03K 3/01 (2006.01)
A61B 8/00 (2006.01)
H03K 17/687 (2006.01)

(52) U.S. Cl.
CPC ........... H03K 3/01 (2013.01); H03K 17/6872 (2013.01); A61B 8/4483 (2013.01)

(58) Field of Classification Search
CPC .... H03K 3/01; H03K 17/6872; A61B 8/4483; H01S 2301/06; H04M 2203/057; H04B 10/2507; H04B 7/005; H04B 7/01; H04B 1/0475; H03F 1/00; H03G 1/00
See application file for complete search history.

(56) References Cited

U.S. PATENT DOCUMENTS

| | | | | |
|---|---|---|---|---|
| 8,670,729 | B2 * | 3/2014 | Behzad | H04B 17/13 |
| | | | | 455/115.2 |
| 10,739,808 | B2 * | 8/2020 | Wan | G05F 3/205 |
| 11,863,170 | B1 * | 1/2024 | Wadekar | H04B 1/04 |
| 2025/0302447 | A1 | 10/2025 | Pattipaka et al. | |

FOREIGN PATENT DOCUMENTS

| | | | | | |
|---|---|---|---|---|---|
| CN | 1930784 | A | * | 3/2007 | .......... H03F 1/0205 |
| DE | 102005061572 | A1 | * | 1/2007 | .......... H04L 27/366 |
| KR | 20160031416 | A | * | 3/2016 | ............ H03F 3/191 |
| WO | WO-2006110590 | A1 | * | 10/2006 | .......... H03M 1/0854 |

* cited by examiner

*Primary Examiner* — Lincoln D Donovan
*Assistant Examiner* — James G Yeaman
(74) *Attorney, Agent, or Firm* — Xianghui Huang; Frank D. Cimino

(57) ABSTRACT

Methods, apparatus, systems, and articles of manufacture are described to correct non-linearity in transmitters. An example system includes an input stage, a driver, an input terminal of the driver coupled to an output terminal of the input stage; an output buffer, an input terminal of the output buffer coupled to an output terminal of the driver, an output terminal of the output terminal coupled to a first input terminal of the input stage via a resistor; and non-linear correction circuitry having an input terminal and an output terminal, the input terminal of the non-linear correction circuitry coupled to the output terminal of the output buffer and the first input terminal of the input stage via the resistor, the output terminal of the non-linear correction circuitry coupled to the output terminal of the input stage and the input terminal of the driver.

20 Claims, 8 Drawing Sheets

HALF WAVE +/- |SCV| GENERATION

METHODS AND APPARATUS TO CORRECT NON-LINEARITY IN TRANSMITTERS

TECHNICAL FIELD

This description relates generally to circuitry, and, more particularly, to methods and apparatus to correct non-linearity in transmitters.

BACKGROUND

Transmitters are electrical devices that transmit, project, or output analog signals. Transmitters are used in a wide range of fields including medical imaging, telecommunications, data transfer, and other fields that utilize analog signals. For example, medical image devices (e.g., ultrasound devices), utilize a transmitter to transmit an ultrasonic analog signal to an object (e.g., an organ). The medical image device obtains from the object a reflection of the transmitted analog signal after transmitting the output analog signal and processes the obtained reflected signal to generate an image of the object.

SUMMARY

For correcting non-linearity in transmitters, an example apparatus includes a first transistor having a control terminal, a first current terminal, and a second current terminal, the control terminal of the first transistor coupled to the second current terminal of the first transistor, the first current terminal of the first transistor coupled to a supply terminal via a first resistor. The apparatus also includes a second transistor having a control terminal, a first current terminal, and a second current terminal, the control terminal of the second transistor coupled to the control terminal of the first transistor and the second current terminal of the first transistor, the first current terminal of the second transistor coupled to the supply terminal via a second resistor and a capacitor. The apparatus also includes a current source having a first terminal and a second terminal, the first terminal of the current source coupled to the control terminals of the first and second transistors, and the second current terminal of the first transistor, the second terminal of the current source coupled to a common terminal. The apparatus also includes a switch having a first terminal and a second terminal, the first terminal of the switch coupled to the second current terminal of the second transistor. Other examples are described.

For correcting non-linearity in transmitters, an example apparatus includes second error current correction circuitry having a first terminal and a second terminal. The apparatus also includes a first switch having a first terminal and a second terminal, the first terminal of the first switch coupled to the second terminal of the first error current correction circuitry, the second terminal of the first switch coupled to the second terminal of the second error current correction circuitry. The apparatus also includes a second switch having a first terminal and a second terminal, the first terminal of the second switch is coupled to the second terminal of the first switch and the second terminal of the second error current correction circuitry, the second terminal of the second switch coupled to a current buffer. The apparatus also includes a resistor having a first terminal and a second terminal, the first terminal of the resistor coupled to the second terminal of the first error current correction circuitry and the first terminal of the first switch, the second terminal of the resistor coupled to a common terminal. The apparatus also includes a capacitor having a first terminal and a second terminal, the first terminal of the capacitor coupled to the second terminal of the first error current correction circuitry, the first terminal of the first switch, and the first terminal of the resistor, the second terminal of the capacitor coupled to the second terminal of the second switch and the current buffer. Other examples are described.

For correcting non-linearity in transmitters, an example transmitter includes an input stage having a first input terminal, a second input terminal and an output terminal. The transmitter also includes a driver having an input terminal and an output terminal, the input terminal of the driver coupled to the output terminal of the input stage. The transmitter also includes an output buffer having an input terminal and an output terminal, the input terminal of the output buffer coupled to the output terminal of the driver, the output terminal of the output terminal coupled to the first input terminal of the input stage via a resistor. The transmitter also includes non-linear correction circuitry having an input terminal and an output terminal, the input terminal of the non-linear correction circuitry coupled to the output terminal of the output buffer and the first input terminal of the input stage via the resistor, the output terminal of the non-linear correction circuitry coupled to the output terminal of the input stage and the input terminal of the driver. Other examples are described.

BRIEF DESCRIPTION OF THE DRAWINGS

The same reference numbers or other reference designators are used in the drawings to designate the same or similar (functionally or structurally) features.

DETAILED DESCRIPTION

Figure 1:
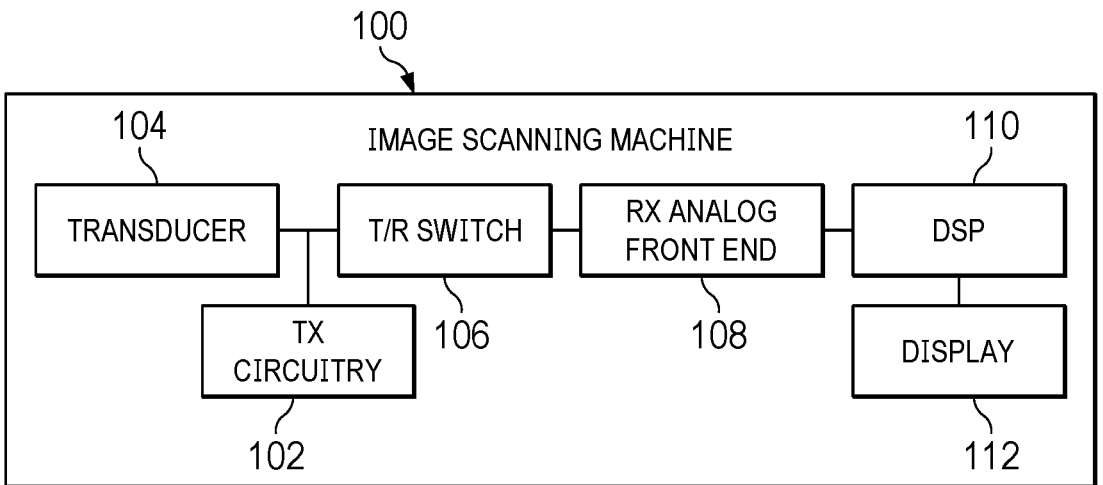
FIG. 1 is an example imaging scanning machine including transmitter circuitry in conjunction with examples described herein.

The drawings are not necessarily to scale. Generally, the same reference numbers in the drawing(s) and this description refer to the same or like parts. Although the drawings show regions with clean lines and boundaries, some or all of these lines or boundaries may be idealized. In reality, the boundaries or lines may be unobservable, blended or irregular.

Medical imaging devices, such as ultrasound devices, utilize transmitted and reflected analog signals to generate images of objects (e.g., organs). For example, an ultrasound device uses a transmitter (also referred to as transmitter circuitry) to transmit ultrasonic wave pulses to the object. After transmitting the ultrasonic waves, the ultrasound device uses a receiver to obtain a reflected echo wave and process the obtained echo wave to image the object.

The transmitter of a medical imaging device is designed to have good second harmonic distortion (HD2) performance. HD2 is a ratio of the second-order harmonic amplitude to the first order amplitude of the medical imaging device pulser output, also known as the fundamental frequency. To achieve good HD2 performance, medical imaging devices select an input frequency (e.g., fin) for the transmitted signal.

As the transmitted ultrasound signal propagates through media, the signal attenuation over the depth of propagation is proportional to fin. The higher fin yields better the resolution of the object represented by the reflection, but higher fin results in a shallower depth the signal can penetrate into the object. After a transmitter outputs a signal with a fin frequency, the object reflects a 2*fin echo signal back to the medical imaging device.

Some transmitters include a linear amplifier to generate the ultrasonic wave that is transmitted to the object during imaging. The linear amplifier may include a signal generator to generate a low voltage analog signal, a transconductor that generates low impedance at a virtual ground and sense error current, a high voltage driver to increase the gain of the sensed error current, and an output buffer to drive the output signal. However, such transmitters may result in undesirable non-linearity. Non-linearity is generated from non-linear active devices, such as transistors, capacitors, etc. that introduce distortions to the output signal of the amplifier. For example, linear amplifiers can operate using a large voltage supply (e.g., +/−100 Volts (V)) based on high load currents (e.g., +/−3 amperes (A)). Accordingly, such linear amplifiers need to use large, high voltage (e.g., 200 V) transistors to operate with the large voltage supply. Such high voltage transistors correspond to low quiescent current for lower power. Large current drawn at the output buffer with small quiescent current leads to large nonlinear errors at the output buffer. A large transistor with small quiescent current leads to low loop bandwidth for the feedback loop that identifies the error current. Thus, the feedback loop of such transmitter is limited, slow, and inaccurate for high bandwidth applications. Dominant nonlinear errors in the transmitter are rectified errors because the signal current in the output buffer is much larger than a bias current in the output buffer. For example, rectified errors are errors caused by the sourcing and sinking of high currents at the output buffer, mismatch between source error and sink error, etc.

Examples described herein provide techniques for reducing, or otherwise eliminating, nonlinearity in a linear amplifier. For example, examples described herein insert a signal into the linear amplifier to mitigate against measured non-linearity during manufacturing. For example, during manufacturing, the nonlinearity of a transmitter can be measured, and a signal can be input into a node of the linear amplifier to mitigate the measured nonlinearity. Examples described herein mitigate rectified capacitive current nonlinear error (|SCV|, where S is the complex frequency of a Laplace transform, C is capacitance, V is the output voltage of an output stage, and SCV corresponds to a current through a capacitive element), capacitive current of rectified voltage nonlinear error (SC|V|), and frequency squared nonlinear error (ST*|SCV|, where T is a time constant). The rectified capacitive current error is error rectification that occurs on current in the output buffer. The error rectification can occur based on gain error between sourcing and sinking paths of the high voltage driver and the output buffer. The capacitive current of rectified voltage nonlinear error can occur at the high voltage switch. The capacitive current of rectified voltage nonlinear error will be 90 degrees out of phase with the rectified capacitive current error. The frequency squared nonlinear error is an error magnitude proportional to the square of the frequency of the input signal. The frequency squared nonlinear error can occur from the delay/phase error between the sourcing and sinking paths of the high voltage driver and the output buffer. Examples described herein result in around an 8 to 10 decibels (dB) improvement in linearity. Also, examples described herein improve HD2 from 40 decibels relative to carrier (dBc) to 50 dBc. Although examples described herein are described in conjunction with an imagine scanning machine, the transmitter or linear amplifier can be described in conjunction with any technology where a transmitter or linear amplifier with nonlinear error is used.

FIG. 1 illustrates an example image scanning machine 100. The image scanning machine 100 of FIG. 1 includes an example transducer 104, example transmitter (Tx) circuitry 102, an example transmitter receiver (T/R) switch 106, an example receiver (Rx) analog front end 108, an example digital signal processor (DSP) 110, and example display 112. The image scanning machine 100 of FIG. 1 is a medical image scanning machine, for example a magnetic resonance imaging (MRI) machine, an ultrasound machine, etc. However, the image scanning machine 100 may be any type of image scanning machine or any device that utilizes a Tx circuitry.

The Tx circuitry 102 of FIG. 1 is coupled to the transducer 104 and the T/R switch 106. The Tx circuitry 102 includes a linear amplifier that amplifies an analog signal that is output to the transducer 104. The linear amplifier utilizes negative feedback to reduce errors in the output signal of the linear amplifier. Also, the Tx circuitry 102 utilizes nonlinear correction circuitry to reduce the nonlinearity of the linear amplifier implemented by if Tx circuitry 102. The Tx circuitry 102 is further described below in conjunction with FIG. 2.

The transducer 104 of FIG. 1 is coupled to the Tx circuitry 102 and the T/R switch 106. The transducer 104 is a device that transmits signals and receives reflected signals to generate an image. For example, in an ultrasound system, the transducer 104 transmits signals (e.g., sound waves, ultrasonic waves, etc.) into a body. After transmitting the ultrasonic waves, the transducer 104 receives or senses reflected waves, also referred to as echo waves or reflected waves, which reflect off tissues of the body. In an MRI system, the transducer 104 may generate a magnetic field and detect the energy released as protons realign with the magnetic field. The transducer 104 transmits one or more analog signals corresponding to an image to the Rx analog front end 108.

The T/R switch 106 of FIG. 1 is coupled to the transducer 104, the Tx circuitry 102 and the Rx analog front end 108. The T/R switch 106 can be disabled to create an open circuit between the transducer 104/Tx circuitry 102 and the Rx analog front end 108 if the Tx circuitry 102 is generating an output signal to be output by the transducer 104. In this manner, if the Tx circuitry 102 is outputting a high voltage analog signal to the transducer 104, the Rx analog front end 108, the DSP 110, and the display 112 are protected from the high voltage(s) output by the Tx circuitry 102. After the Tx circuitry 102 stops outputting a high voltage analog signal to the transducer 104, the T/R switch 106 enables to create a short between the transducer 104 and the Rx analog front end 108. In this manner, the Rx analog front end 108 can obtain an echo signal obtained at the transducer 104.

The Rx analog front end 108 of FIG. 1 is coupled to the T/R switch 106 and the DSP 110. The Rx analog front end 108 is an instrumentation amplifier topology that amplifies the signal from the transducer 104 and converts the analog echo signal to a digital signal. The Rx analog front end 108 outputs the amplified digital signals to DSP 110.

The DSP 110 of FIG. 1 is coupled to the Rx analog front end 108 and the display 112. The DSP 110 processes the digital signals from the Rx analog front end 108 to generate an image of the object sensed by the transducer 104. The DSP 110 outputs the generated image to the display 112. Also, the DSP 110 can store the image data, or any data related to the capture of the image into storage (e.g., memory).

Figure 2:
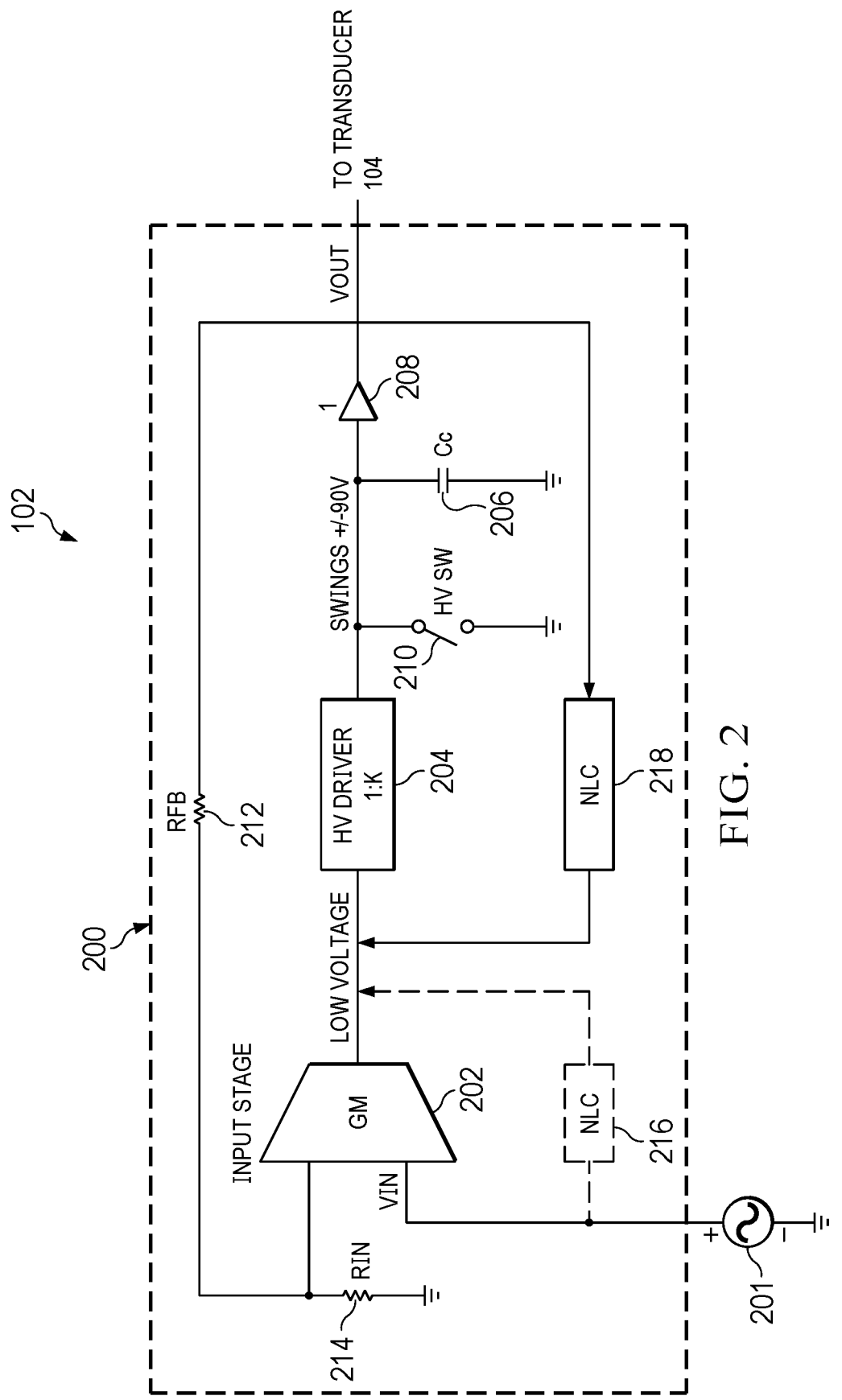
FIG. 2 is a diagram of an example circuit implementation of the transmitter circuitry of FIG. 1.

FIG. 2 is an example implementation of the transmitter circuitry 102 of FIG. 1. The transmitter circuitry 102 includes an example linear amplifier 200 and example signal generation circuitry 201. The linear amplifier 200 includes an example input stage 202, an example high voltage (HV) driver 204, an example capacitor 206, an example output stage 208, an example high voltage (HV) switch 210, example resistors 212, 214, and example nonlinear correction (NLC) circuitry 216, 218.

The signal generator circuitry 201 of FIG. 1 includes two terminals. The first terminal of the signal generator circuitry 201 is coupled to the second input terminal of the input stage 202. The second terminal of the signal generator circuitry 201 is coupled to a common terminal (e.g., a ground terminal). The signal generator circuitry 201 generates an analog signal. The analog signal may be a low voltage analog signal (e.g., +/−5 V). In some examples, the signal generator circuitry 201 is located outside of the transmitter circuitry 102. In such examples, the transmitter circuitry 102 includes an input terminal to obtain the analog signal from the signal generation circuitry implemented outside of the transmitter circuitry 102.

The input stage 202 of FIG. 2 includes a first input terminal, a second input terminal, and an output terminal. The first input terminal of the input stage 202 is coupled to the second terminal of the resistor 212 and the first terminal of the resistor 214. The second input terminal of the input stage 202 is coupled to the second terminal of the signal generator circuitry 201. In some examples, the second input terminal of the input stage 202 is coupled to the input terminal of the NLC circuitry 216. The output terminal of the input stage 202 is coupled to the input terminal of the HV driver 204 and the output terminal of the NLC circuitry 218. In some examples, the output terminal of the input stage 202 is coupled to the output terminal of the NLC circuitry 216. The input stage 202 is a transconductor that compares the voltage of the output signal output by the signal generator circuitry 201 to a feedback voltage corresponding to the output signal of the output stage 208. The input stage outputs a current representative of a difference between the two output voltages. The output current of the input stage 202 is representative of an error between the input signal of the signal generation circuitry 201 and the output signal of the output stage 208. The larger the error between the input signal and the output signal, the larger the output current. The smaller the error between the input signal and the output signal, the smaller the output current.

The HV driver 204 of FIG. 2 includes an input terminal and an output terminal. The input terminal of the HV driver 204 is coupled to the output terminal of the input stage 202, the output terminal of the NLC 218, and, optionally, the output terminal of the NLC circuitry 216. The output terminal of the HV driver 204 is coupled to the first terminal of the HV switch 210, the first terminal of the capacitor 206, and the input terminal of the output stage 208. The HV driver 204 increases the gain (e.g., by a factor of K) of the error signal output by the input signal 202, which is adjusted by the one or more NLC circuitry 216, 218. The amount of gain may be based on user or manufacturer preferences. The HV driver 204 outputs the amplified error signal to the output stage 208.

The capacitor 206 of FIG. 2 includes a first terminal and a second terminal. The first terminal of the capacitor 206 is coupled to the output terminal of the HV driver 204, the input terminal of the output stage 208 and the first terminal of the HV switch 210. The second terminal of the capacitor 206 is coupled to the common terminal (e.g., the ground terminal). The capacitor 206 acts as a compensation capacitor and filters out high frequency noise.

The example output stage 208 of FIG. 2 includes an input terminal and an output terminal. The input terminal of the output stage 208 is coupled to the output terminal of the HV driver 204, the first terminal of the capacitor 206, and the first terminal of the switch 210. The output terminal of the output stage 208 is coupled to the first terminal of the resistor 212, the input terminal of the NLC circuitry 218, and the transducer 104. The output stage 208 operates as a voltage buffer to drive the load of the transducer 104. As further described above, the HV driver 204 and the output stage 208 can generate nonlinearity error (e.g., |SCV| error, SC|V| error, and ST*|SCV| error) that is reduced by the NLC circuitry 216, 218.

The HV switch (HV SW) 210 of FIG. 2 includes a first terminal and a second terminal. The first terminal of the HV SV 210 is coupled to the output terminal of the HV driver 204, the input terminal of the output stage 208, and the first terminal of the capacitor 206. The second terminal of the HV SW 210 is coupled to the common terminal. The HV SW 210 provides glitch reduction during power up and power down of the image scanning machine 100.

The resistors 212, 214 of FIG. 2 each include a first terminal and a second terminal. The first terminal of the resistor 212 is coupled to the output terminal of the output stage 208, the input terminal of the NLC circuitry 218, and the transducer 104. The second terminal of the resistor 212 is coupled to the first terminal of the resistor 214 and the first input terminal of the input stage 202. The first terminal of the resistor 214 is coupled to the second terminal of the resistor 212 and the first input terminal of the input stage 202. The second terminal of the resistor 214 is coupled to the common terminal. The resistors 212, 214 create a feedback path from the output stage 208 to the input stage 202. Also, the resistors 212, 214 reduce the amplitude or voltage of the output stage 208 to the amplitude of the signal output by of the signal generation circuitry 201. In this manner, if there is no error between the input signal of the signal generation circuitry 201 and the output signal of the output stage 208, the input stage 202 will detect zero error current and output a signal corresponding to zero error current. However, if there is some difference between the input signal of the signal generation circuitry 201 and the output signal of the output stage 208, the input stage 202 will output a signal corresponding to the amount of difference. As described above, the HV driver 204 increases the gain of the error signal and the output stage 208 outputs a signal based on the amplified error signal to drive the transducer 104.

The NLC circuitry 216 of FIG. 1 is an optional component that can be implemented to mitigate some nonlinearity error. The NLC circuitry 216 includes an input terminal and an output terminal. The input terminal of the NLC circuitry 216 is coupled to the output terminal of the signal generation circuitry 201 and the second input terminal of the input stage 202. The output terminal of the NLC circuitry 216 is coupled to the output terminal of the input stage 202, the input terminal of the HV driver 204 and the output terminal of the NLC 218. The NLC circuitry 216 introduces nonlinearity to the output of the input stage 202 based on the input signal generated by the signal generation circuitry 201 to mitigate a measured non-linearity at the output of the linear amplifier 200. For example, during manufacturing, the nonlinearity of the linear amplifier 200 is determined and the gain associated with the components of the NLC circuitry 216 is adjusted to mitigate the output of the input stage 202 based on the input signal generated by the signal generator circuitry 201. Although the NLC circuitry 216 mitigates some nonlinearity, the NLC circuitry 216 may be less effective for low bandwidth amplifiers. Also, nonlinearity is a strong function of the output signal. Accordingly, the example NLC circuitry 218 is implemented to provide a strong mitigation to nonlinearity, which is also effective for low BW amplifiers.

The example NLC circuitry 218 of FIG. 2 includes an input terminal and an output terminal. The input terminal of the NLC circuitry 218 is coupled to the output terminal of the output stage 208, the first terminal of the resistor 212, and the transducer 104. The output terminal of the NLC circuitry 218 is coupled to the output terminal of the input stage 202, the input terminal of the HV driver 204, and, optionally, the output terminal of the NLC circuitry 216. The NLC circuitry 218 of FIG. 2 generates a signal to mitigate nonlinearity based on the output of the linear amplifier 200 as part of a feedback loop. The NLC circuitry 218 generates signal(s) that mitigate for the different nonlinear current errors (e.g., [SCV], SC|V|, ST*|SVC|) based on the output of the linear amplifier 200. The NLC circuitry 218 senses the high voltage output and generates low voltage signals whose magnitude and phase is proportional to the output signal of the linear amplifier 200. The magnitude of the mitigating signal(s) is/are based on a gain selected during manufacturing based on the measured nonlinearity of the linear amplifier 200. The NLC circuitry 218 is further described below in conjunction with FIG. 3.

Figure 3:
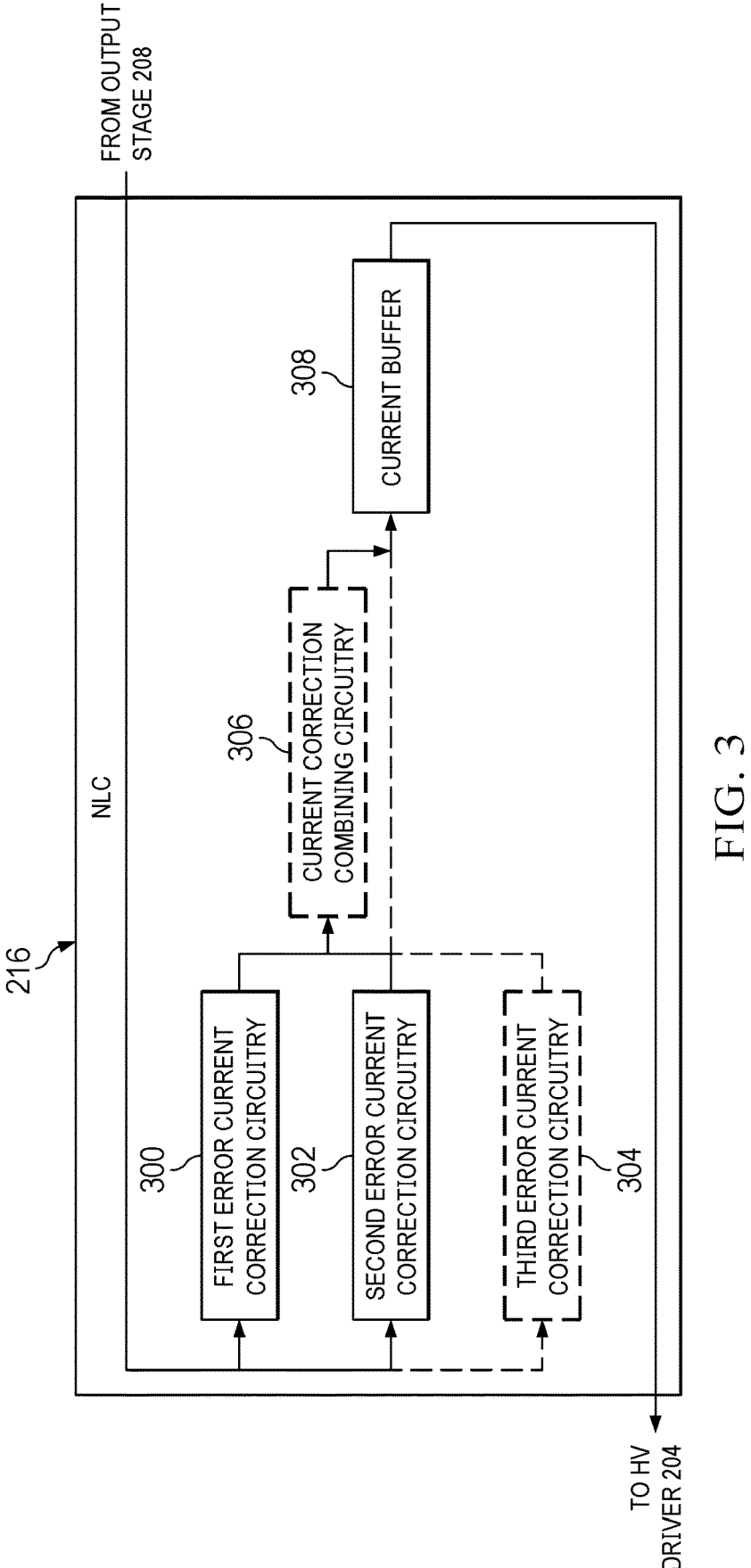
FIG. 3 is a diagram of an example circuit implementation of non-linear correction circuitry of FIG. 2.

FIG. 3 is an example block diagram of the NLC circuitry 216 of FIG. 2. The NLC circuitry 216 includes example first error current correction circuitry 300, example second error current correction circuitry 302, example third current correction circuitry 304, example current correction combining circuitry 306, and an example current buffer 308.

The first error current correction circuitry 300 of FIG. 3 includes an input terminal and an output terminal. The input terminal of the first error current correction circuitry 300 is coupled to the output stage 208 of FIG. 2. In some examples, the output terminal of the first error current correction circuitry 300 is coupled to the current correction combining circuitry 306. In some examples, the output terminal of the first error correction circuitry 300 is coupled to the output terminal of the second error current correction circuitry 302, the output terminal of the third error current correction circuitry 304, and the input terminal of the current buffer 308. The first error current correction circuitry 300 generates a signal corresponding to a rectified capacitive current (|SCV|) error that occurs from gain differences between sourcing and sinking paths of the HV driver 204 and the output stage 208 of FIG. 2. The first error current correction circuitry 300 generates the signal in phase with the rectified capacitive error current. After the amount of |SCV| nonlinear error is determined during manufacturing, the gain of the first error current correction circuitry 300 can be selected to mitigate the |SCV| error, which is applied to input terminal of the HV driver 204 via a feedback path, as described above in conjunction with FIG. 2. The first error current correction circuitry 300 is further described below in conjunction with FIG. 4.

The second error current correction circuitry 302 of FIG. 3 includes an input terminal and an output terminal. The input terminal of the second error current correction circuitry 302 is coupled to the output stage 208 of FIG. 2. In some examples, the output terminal of the second error current correction circuitry 302 is coupled to the current correction combining circuitry 306. In some examples, the output terminal of the second error current correction circuitry 302 coupled to the output terminal of the first error current correction circuitry 300, the output terminal of the third error current correction circuitry 304, and the input terminal of the current buffer 308. The second error current correction circuitry 302 generates a signal corresponding to a capacitive current of rectified voltage (SC|V|) error that occurs from the HV driver 204. The error is 90 degrees out of phase with the |SCV| error. This, the second error current correction circuitry 302 generates the signal in 90 degrees out of phase of the |SCV| error current. After the amount of SC|V| nonlinear error is determined during manufacturing, the gain of the second error current correction circuitry 302 can be selected to mitigate the SC|V| error, which is applied to input terminal of the HV driver 204 via a feedback path, as described above in conjunction with FIG. 2. Because the mitigation signals generated by the first and second error current correction circuitries 302 corresponds to phases that are 90 degrees apart, the first and second error correction circuitries 302 can mitigate for any phase error by adjusting magnitude of the two generated mitigation signal. The second error current correction circuitry 302 is further described below in conjunction with FIG. 5.

The third error current correction circuitry 304 of FIG. 3 includes an input terminal and an output terminal. The input terminal of the third error current correction circuitry 304 is coupled to the output stage 208 of FIG. 2. The output terminal of the third error correction circuitry 304 is coupled to the output terminal of the first error current correction circuitry 300, the output terminal of the second error current correction circuitry 302, and the input terminal of the current buffer 308. The third error current correction circuitry 304 generates a signal corresponding to a frequency squared (ST*|SCV|) error that occurs from delay or phase differences between sourcing and sinking paths of the HV driver 204 and the output stage 208 of FIG. 2 and because error magnitude is proportional to frequency squared. After the amount of ST*|SCV| nonlinear error is determined during manufacturing, the gain of the third error current correction circuitry 304 can be selected to mitigate the ST*|SCV| error, which is applied to input terminal of the HV driver 204 via a feedback path, as described above in conjunction with FIG. 2. The third error current correction circuitry 304 is further described below in conjunction with FIG. 6.

The current correcting combining circuitry 306 of FIG. 3 is optional circuitry that can be implemented to eliminate the third current correction circuitry 304 but keep the functionality. Accordingly, if the current correction combining circuitry 306 is implemented, the third error current correction circuitry 304 can be removed while the functionality of the third error current correction circuitry 304 is maintained. The current correction combining circuitry 306 includes an input terminal and an output terminal. The input terminal of the current correction combining circuitry 306 is coupled to the output terminal of the first error current correction circuitry 300 and the output terminal of the second error current correction circuitry 302. The output terminal of the current correction combining circuitry 306 is coupled to the input terminal of the current buffer 308. The current correction combining circuitry 306 is further described below in conjunction with FIG. 7.

The current buffer 308 of FIG. 3 includes an input terminal and an output terminal. The input terminal of the current buffer 308 is coupled to the output terminal of the current correction combining circuitry 306. Alternatively, the input terminal of the current buffer 308 can be coupled to the output terminals of the error current correction circuitries 300, 302, 304. The output terminal of the current buffer 308 is coupled to the output terminal of the input stage 202, the input terminal of the HV driver 204, and, optionally, the output terminal of the NLC circuitry 216. The current buffer 308 blocks the output signal from input stage 202 or the output signal from the NLC circuitry 216 from entering the error current correction circuitries 300, 302, 304 and the current correction combining circuitry 306.

Figure 4:
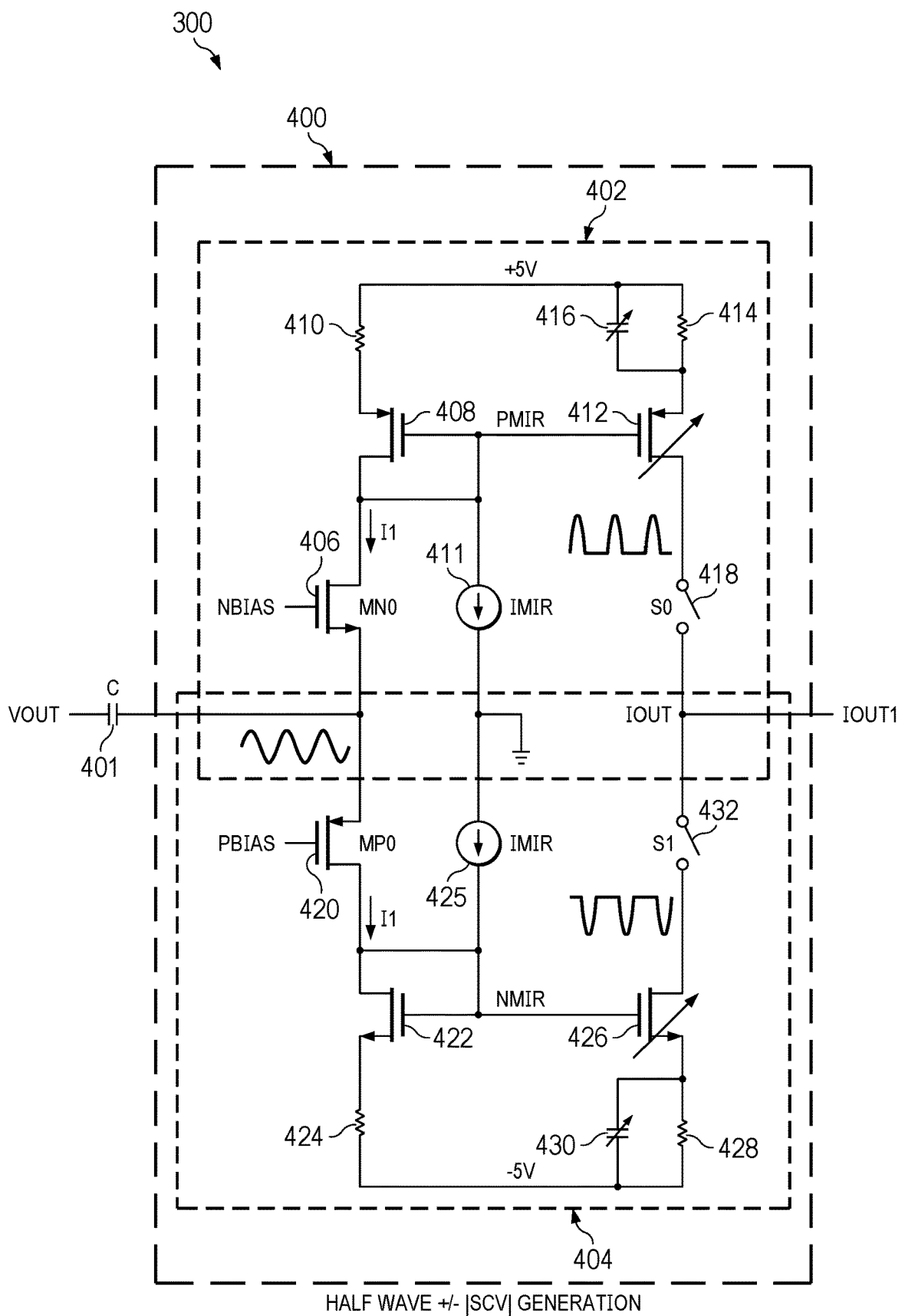
FIG. 4 is a diagram of an example circuit implementation of first error current correction circuitry of FIG. 3.

FIG. 4 is an example circuit implementation of the first error current correction circuitry 300 of FIG. 3. The first error current correction circuitry 300 includes an example current rectifier 400 and an example capacitor 401. The current rectifier 400 includes a positive current rectifier 402 and a negative current rectifier 404. The positive current rectifier 402 includes transistors 406, 408, 412, resistors 410, 414, a current source circuitry 411, a capacitor 416, and a switch 418. The negative current rectifier 402 includes transistors 420, 422, 426, resistors 424, 428, a current source circuitry 425, a capacitor 430, and a switch 432.

The capacitor 401 of FIG. 4 is a sensing capacitor that includes an input terminal and an output terminal. The input terminal of the capacitor 401 is coupled to the output terminal of the output stage 208, the first terminal of the resistor 212, and the transducer 104. The output terminal of the capacitor 401 is coupled to the second current terminal of the transistor 406 and the first current terminal of the transistor 420. The current through the capacitor 401 is represented by SCV (e.g., the complex frequency of the Laplace transform time the capacitance of the capacitor 401). The sensed current is applied to the current rectifier 400.

The current rectifier 400 of FIG. 4 includes the positive current rectifier 402 and the negative current rectifier 404. The positive current rectifier 402 generates a positive rectified signal (e.g., absolute value signal) corresponding to the positive portion of the input current (e.g., where the negative portion is zeroed out). The negative current rectifier 404 generates a negative rectified signal (e.g., a negative absolute value signal) corresponding to the negative portion of the input current (e.g., where the positive portion is zeroed out).

The positive current rectifier 402 of FIG. 4 includes a transistor 406 to rectify the sensed current from the capacitor 401. The transistor 406 includes a control terminal (e.g., a gate terminal), a first current terminal (e.g., a drain terminal), and a second current terminal (e.g., a source terminal). The control terminal of the transistor 406 is coupled to a bias current source. The bias current source provides low quiescent current (e.g., less than 1 microamperes (uA)) to bias the transistor 406. The first current terminal of the transistor 406 is coupled to the second current terminal of the transistor 408, the control terminals of the transistors 408, 412, and the first terminal of the current source circuitry 411. The second current terminal of the transistor 406 is coupled to the second terminal of the capacitor 401 and the first current terminal of the transistor 420. The transistor 406 is an n-channel metal oxide semiconductor field effect (NMOS or N-MOSFET) transistor. However, the transistor 406 may be a different type of transistor. The transistor 406 is biased based on a low quiescent current (e.g., less than 1 microamperes (uA)) provided by a bias current source. The transistor 406 rectifies the sensed current to allow the current to flow from the first current terminal of the transistor 406 to the second current terminal of the transistor 406 for the positive portion of the sensed current (e.g., blocking the negative portion of the sensed current).

The transistors 408, 412 of FIG. 4 each include a control terminal (e.g., a gate terminal), a first current terminal (e.g., a source terminal), and a second current terminal (e.g., a drain terminal). The control terminal of the transistor 408 is coupled to the control terminal of the transistor 412, the second current terminal of the transistor 408, the first current terminal of the transistor 406, and the first terminal of the current source circuitry 411. The first current terminal of the transistor 408 is coupled to the second terminal of the resistor 410. The second current terminal of the transistor 408 is coupled to the control terminals of the transistors 408, 412, the first current terminal of the transistor 406, and the first terminal of the current source circuitry 411. The control terminal of the transistor 412 coupled to the control terminal of the transistor 408, the second current terminal of the transistor 408, the first current terminal of the transistor 406, and the first terminal of the current source circuitry 411. The first current terminal of the transistor 412 is coupled to the second terminal of the capacitor 416 and the second terminal of the resistor 414. The second terminal of the transistor 412 coupled to the first terminal of the switch 418. The transistors 408, 412 are p-channel MOSFETs (e.g., PMOS transistors). However, the transistors 408, 412 can be any type of transistor. The transistors 408, 412 are structured to operate as a current mirror. Accordingly, the current flowing from the second terminal of the transistor 412 to the first terminal of the switch 418 is proportional (e.g., with the same or a different gain) to the current flowing from the second current terminal of the transistor 408 to the first current terminal of the transistor 406. Accordingly, if the switch 418 is closed (e.g., creating a short circuit), the output current of the current rectifier 400 corresponds to the positive rectified current based on the current through the capacitor 401. The amount of gain of the current mirror corresponding to transistors 408, 412 is based on the capacitance of the capacitor 416 and the size (e.g., channel width and length) of the transistor 412. Also, programmable capacitance can be used to adjust the capacitance of the capacitor 430 for phase adjustment for trimming. The amount of capacitance or size of the transistor 412 can be selected to correspond to an amount of detected nonlinearity during manufacturing. In this manner, the current output can mitigate the detected |SCV| nonlinearity. In FIGS. 4, 5, 6, 7, and 8, the diagonal arrow through a component indicates that the amount of capacitance or the size of the component can be selected to correspond to an amount of detected nonlinearity during manufacturing.

The current source circuitry 411 of FIG. 4 includes a first terminal and a second terminal. The first terminal of the current source circuitry 411 is coupled to the control terminals of the transistors 408, 412. The second terminal of the current source circuitry 411 is coupled to the second terminal of the current source circuitry 425 and a common terminal. The current source circuitry pulls a small current (e.g., 100 uA) to ground to reduce a mirror delay minimum current corresponding to the current mirror generated by the transistors 408, 412.

The resistors 410, 414 and the capacitor 416 each have a first terminal and a second terminal. The first terminal of the resistor 410 is coupled to a positive supply terminal (e.g., +5 V). The second terminal of the resistor 410 is coupled to the first current source of the transistor 408. The first terminal of the resistor 414 is coupled to the positive supply terminal. The second terminal of the resistor 410 is coupled to the first current terminal of the transistor 412 and the second terminal of the capacitor 416. The first current terminal of the capacitor 416 is coupled to the positive supply terminal. The second current terminal of the capacitor 416 is coupled to the second terminal of the resistor 414 and the first current terminal of the transistor 412. The resistance of the resistor 414, or the size of the transistor 412 can be combined as a unit to adjust the gain. Also, the resistor 414 creates a phase lead. The resistors 410, 414 improve noise and matching.

The switch 418 of FIG. 4 includes a first terminal and a second terminal. The first terminal of the switch 418 is coupled to the second current terminal of the transistor 412. The second terminal of the switch 418 can be (e.g., depending on the implementation of the NLC circuitry 216 of FIG. 3) coupled to the first terminal of the switch 432, the output terminals(s) of the second current second and third error current correction circuitries 302, 304, the current correction combining circuitry 306, or the input terminal of the current buffer 308. The switch 418 may be a MOSFET (e.g., a PMOS or an NMOS) or any other switch. If the switch is turned off or disabled (e.g., creating an open circuit), the positive rectified current is blocked or not output at the output terminal of the first error current correction circuitry 300. If the switch is turned on or enabled (e.g., creating a short circuit), the positive rectified current is passed to the output terminal of the first error current correction circuitry 300. For example, during manufacturing, if a negative |SCV| error is detected, the switch 418 can be enabled so that the positive rectified current can be fed into the feedback loop to mitigate the detected negative |SCV| error. However, if the |SCV| error is positive, the switch 418 may be disabled and the switch 432 may be enabled to mitigate the positive |SCV| error, as further described below.

The negative current rectifier 404 of FIG. 4 includes a transistor 420 to rectify the sensed current from the capacitor 401. The transistor 420 includes a control terminal (e.g., a gate terminal), a first current terminal (e.g., a drain terminal), and a second current terminal (e.g., a source terminal). The control terminal of the transistor 420 is coupled to a bias current source. The bias current source provides low quiescent current (e.g., less than 1 microamperes (uA)) to bias the transistor 420. The first current terminal of the transistor 420 is coupled to the second current terminal of the transistor 422, the control terminals of the transistors 422, 426, and the first terminal of the current source circuitry 425. The second current terminal of the transistor 420 is coupled to the second terminal of the capacitor 401 and the second current terminal of the transistor 406. The transistor 420 is a p-channel metal oxide semiconductor field effect (PMOS or P-MOSFET) transistor. However, the transistor 420 may be a different type of transistor. The transistor 420 is biased based on a low quiescent current (e.g., less than 1 microamperes (uA)) provided by a bias current source. The transistor 420 rectifies the sensed current to allow the current to flow from the first current terminal of the transistor 420 to the second current terminal of the transistor 420 for the negative portion of the sensed current (e.g., blocking the positive portion of the sensed current).

The transistors 422, 426 of FIG. 4 each include a control terminal (e.g., a gate terminal), a first current terminal (e.g., a source terminal), and a second current terminal (e.g., a drain terminal). The control terminal of the transistor 422 is coupled to the control terminal of the transistor 426, the second current terminal of the transistor 422, the first current terminal of the transistor 420, and the first terminal of the current source circuitry 425. The first current terminal of the transistor 422 is coupled to the second terminal of the resistor 424. The second current terminal of the transistor 422 is coupled to the control terminals of the transistors 422, 426, the first current terminal of the transistor 420, and the first terminal of the current source circuitry 425. The control terminal of the transistor 426 coupled to the control terminal of the transistor 422, the second current terminal of the transistor 422, the first current terminal of the transistor 420, and the first terminal of the current source circuitry 425. The first current terminal of the transistor 426 is coupled to the second terminal of the capacitor 430 and the second terminal of the resistor 428. The second terminal of the transistor 426 coupled to the first terminal of the switch 432. The transistors 422, 426 are n-channel MOSFETs (e.g., NMOS transistors). However, the transistors 422, 426 can be any type of transistor. The transistors 422, 426 are structured to operate as a current mirror. Accordingly, the current flowing from the second terminal of the transistor 426 to the first terminal of the switch 432 is proportional (e.g., with the same or a different gain) to the current flowing from the second current terminal of the transistor 422 to the first current terminal of the transistor 420. Accordingly, if the switch 432 is closed (e.g., creating a short circuit), the output current of the current rectifier 400 corresponds to the negative rectified current based on the current through the capacitor 401. The amount of gain of the current mirror corresponding to transistors 422, 426 is based on the capacitance of the capacitor 430 and the size (e.g., channel width and length) of the transistor 426. Also, programmable capacitance can be used to adjust the capacitance of the capacitor 430 for phase adjustment for trimming. The amount of capacitance or size of the transistor 426 can be selected to correspond to the amount of detected nonlinearity during manufacturing. In this manner, the current output can mitigate the detected |SCV| nonlinearity.

The current source circuitry 425 of FIG. 4 includes a first terminal and a second terminal. The first terminal of the current source circuitry 425 is coupled to the control terminals of the transistors 422, 426. The second terminal of the current source circuitry 425 is coupled to the second terminal of the current source circuitry 411 and a common terminal. The current source circuitry pulls a small current (e.g., 100 uA) to ground to reduce a mirror delay minimum current corresponding to the current mirror generated by the transistors 422, 426.

The resistors 424, 428 and the capacitor 430 each have a first terminal and a second terminal. The first terminal of the resistor 424 is coupled to a negative supply terminal (e.g., −5 V). The second terminal of the resistor 424 is coupled to the first current source of the transistor 422. The first terminal of the resistor 428 is coupled to the negative supply terminal. The second terminal of the resistor 424 is coupled to the first current terminal of the transistor 426 and the second terminal of the capacitor 430. The first current terminal of the capacitor 430 is coupled to the negative supply terminal. The second current terminal of the capacitor 430 is coupled to the second terminal of the resistor 428 and the first current terminal of the transistor 426. The resistance of the resistor 428, or the size of the transistor 426 can be combined as a unit to adjust the gain. Also, the resistor 428 creates a phase lead. The resistors 424, 428 improve noise and matching.

The switch 432 of FIG. 4 includes a first terminal and a second terminal. The first terminal of the switch 432 is coupled to the second current terminal of the transistor 426. The second terminal of the switch 432 can be (e.g., depending on the implementation of the NLC circuitry 216 of FIG. 3) coupled to the first terminal of the switch 418, the output terminals(s) of the second current second and third error current correction circuitries 302, 304, the current correction combining circuitry 306, or the input terminal of the current buffer 308. The switch 432 may be a MOSFET (e.g., a PMOS or an NMOS) or any other switch. If the switch is turned off or disabled (e.g., creating an open circuit), the negative rectified current is blocked or not output at the output terminal of the first error current correction circuitry 300. If the switch is turned on or enabled (e.g., creating a short circuit), the negative rectified current is passed to the output terminal of the first error current correction circuitry 300. For example, during manufacturing, if a positive |SCV| error is detected, the switch 432 can be enabled so that the negative rectified current can be fed into the feedback loop to mitigate the detected positive |SCV| error. However, if the |SCV| error is negative, the switch 432 may be disabled and the switch 418 may be enabled to mitigate the positive |SCV| error, as further described above.

Figure 5:
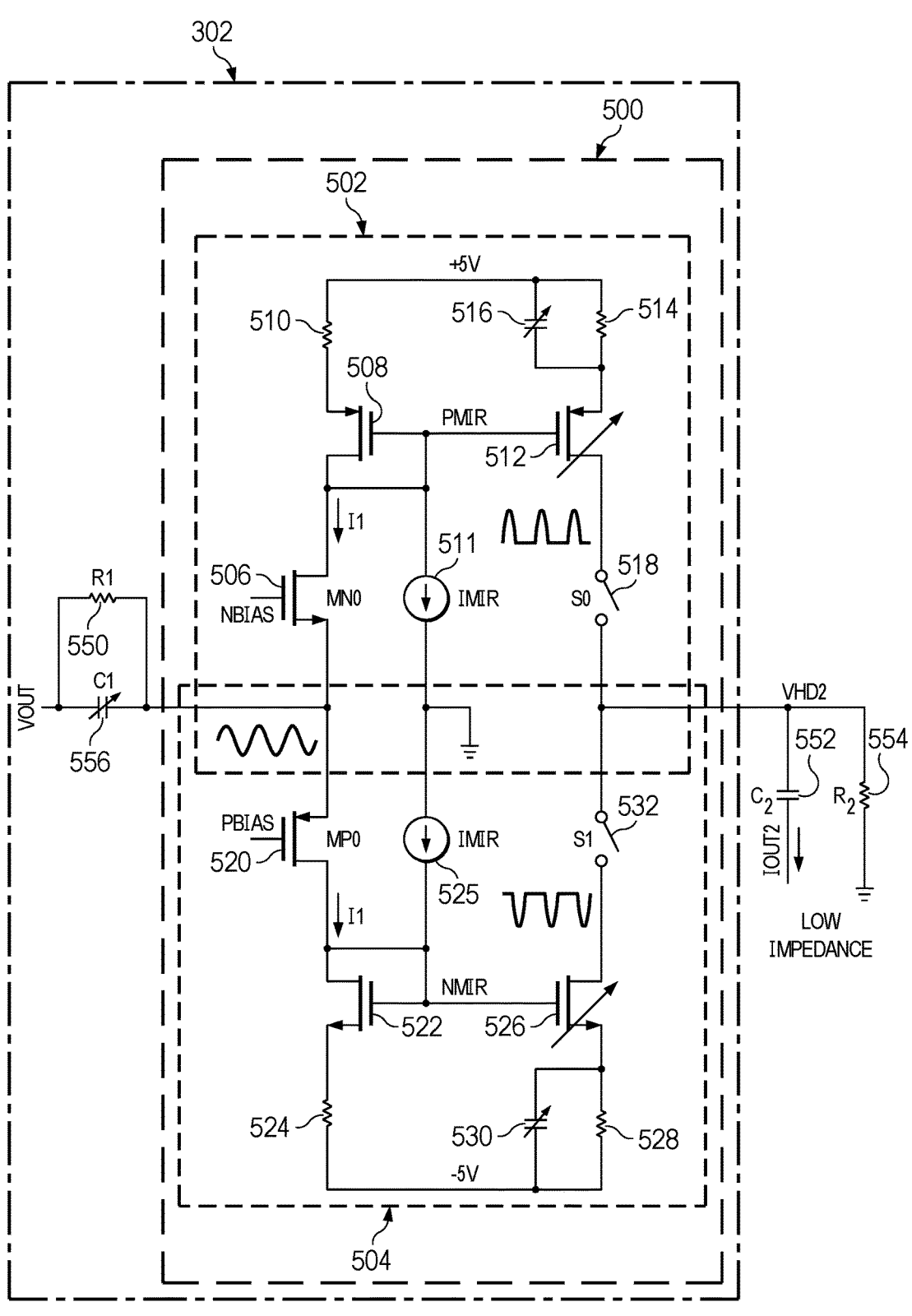
FIG. 5 is a diagram of an example circuit implementation of second error current correction circuitry of FIG. 3.

FIG. 5 is an example circuit implementation of the second error current correction circuitry 302 of FIG. 3. The second error current correction circuitry 302 includes an example current rectifier 500. The current rectifier 500 includes a positive current rectifier 502 and a negative current rectifier 504. The positive current rectifier 502 includes transistors 506, 508, 512, resistors 510, 514, a current source 511, a capacitor 516, and a switch 318. The negative current rectifier 504 includes transistors 520, 522, 526, resistors 524, 528, a current source 525, a capacitor 280, and a switch 532. The second error current correction circuitry 302 further includes the resistor 550 and the capacitor 556. FIG. 5 further includes the example capacitor 552 and the resistor 554. The operation of the current rectifier 500 is same as the current rectifier 400 of FIG. 4. However, the input terminal and the output terminal of the current rectifier 500 of FIG. 5 are coupled to different components than the current rectifier 400 of FIG. 4. Accordingly, for the sake of brevity, because the components of the rectifier 500 corresponds both structurally and functionally to the components of the rectifier 400 of FIG. 4, but for the different input connection and different output connection, the structure and function of the components of the rectifier 500 will not further be described except for the differences to the rectifier 400 of FIG. 4. Further description of the components can be ascertained from the above description in FIG. 4.

The resistors 550, 554 of FIG. 5 each include a first terminal and a second terminal. The first terminal of the resistor 550 is coupled to the output terminal of the output stage 208, the first terminal of the resistor 212, the transducer 104, and the first terminal of the capacitor 556. The second terminal of the resistor 550 is coupled to the second terminal of the capacitor 556, the second current terminal of the transistor 506 and the second current terminal of the transistor 520. The first terminal of the resistor 554 is coupled to the second terminals of the switch 518 and the switch 532 and the first terminal of the capacitor 552. The second terminal of the resistor 554 is coupled to the common terminal.

The capacitors 552, 556 of FIG. 5 each include a first terminal and a second terminal. The first terminal of the capacitor 552 is coupled to the second terminals of the switches 518, 532 and the first terminal of the resistor 554. The second terminal of the capacitor 552 can be (e.g., depending on the implementation of the NLC circuitry 216 of FIG. 3) coupled to the output terminals(s) of the second current first and third error current correction circuitries 300, 304, the current correction combining circuitry 306, or the input terminal of the current buffer 308. The first terminal of the capacitor 556 is coupled to the output terminal of the output stage 208, the first terminal of the resistor 212, the transducer 104, and the first terminal of the resistor 550. The second terminal of the capacitor 556 is coupled to the second terminal of the resistor 550 and the second current terminals of the transistors 506, 520.

The resistor 550 operates as a sense resistor to sense the output voltage corresponding to an input current into the rectifier 500. (e.g., the input current is Vout/R1, where Vout is the output voltage of the output stage 208 and R1 is the resistance of the resistor 550). Because the rectifier 500 rectifies the input current, the rectifier 500 pumps a rectified current (e.g., |Vout/R1|) into the resistor 554 to generate output voltage (VHD2) of the rectifier 500 (e.g., VHD2=|Vout/R1|*R2=K*|Vout|, where R2 is the resistance of the resistor 554 and K=R2/R1). The capacitor 552 obtains the received output voltage to generate the SC|V| error current (Iout2) (e.g., Iout2=SC2*K*|Vout|, where C2 is the capacitance of the capacitor 552), ignoring the capacitor 556. The capacitor 556 compensates for the phase lag generated by the capacitor 552. However, adding the capacitor 552 to the output of the rectifier 500 adds a pole that can lead to phase error in correction current. Accordingly, the capacitor 556 is connected in parallel with the resistor 550 to compensate phase error coming from a pole by adding a zero. Thus, the output current (Iout2) of the second current error current correction circuitry 302 is shown in the below Equation 1.

$$Iout2 = \left| Vout * \left( \frac{1 + SR_1C_1}{R_1} \right) \right| * \left( \frac{SR_2C_2}{1 + SR_2C_2} \right) \approx \qquad \text{(Equation 1)}$$
$$SC_2 * |Vout| * (R_2/R_1) \text{ for } R_1C_1 \approx R_2C_2$$

As described above, the SC|V| current can be used to mitigate SC|V| nonlinear error. For example, during manufacturing the SC|V| nonlinear error can be determined. Accordingly, the resistances of the resistors 514, 528, 550, 554, the capacitance of the capacitors 516, 530, 552, 556, the size of the transistors 512, 526, or the operation of the switches 518, 532 can be selected to generate an SC|V| error mitigation signal that is fed back into the HV driver 204 to mitigate the determined SC|V| error. As described above, the SC|V| signal is 90 degrees out of phase with the |SCV| signal generated by the first error current correction circuitry 300.

Figure 6:
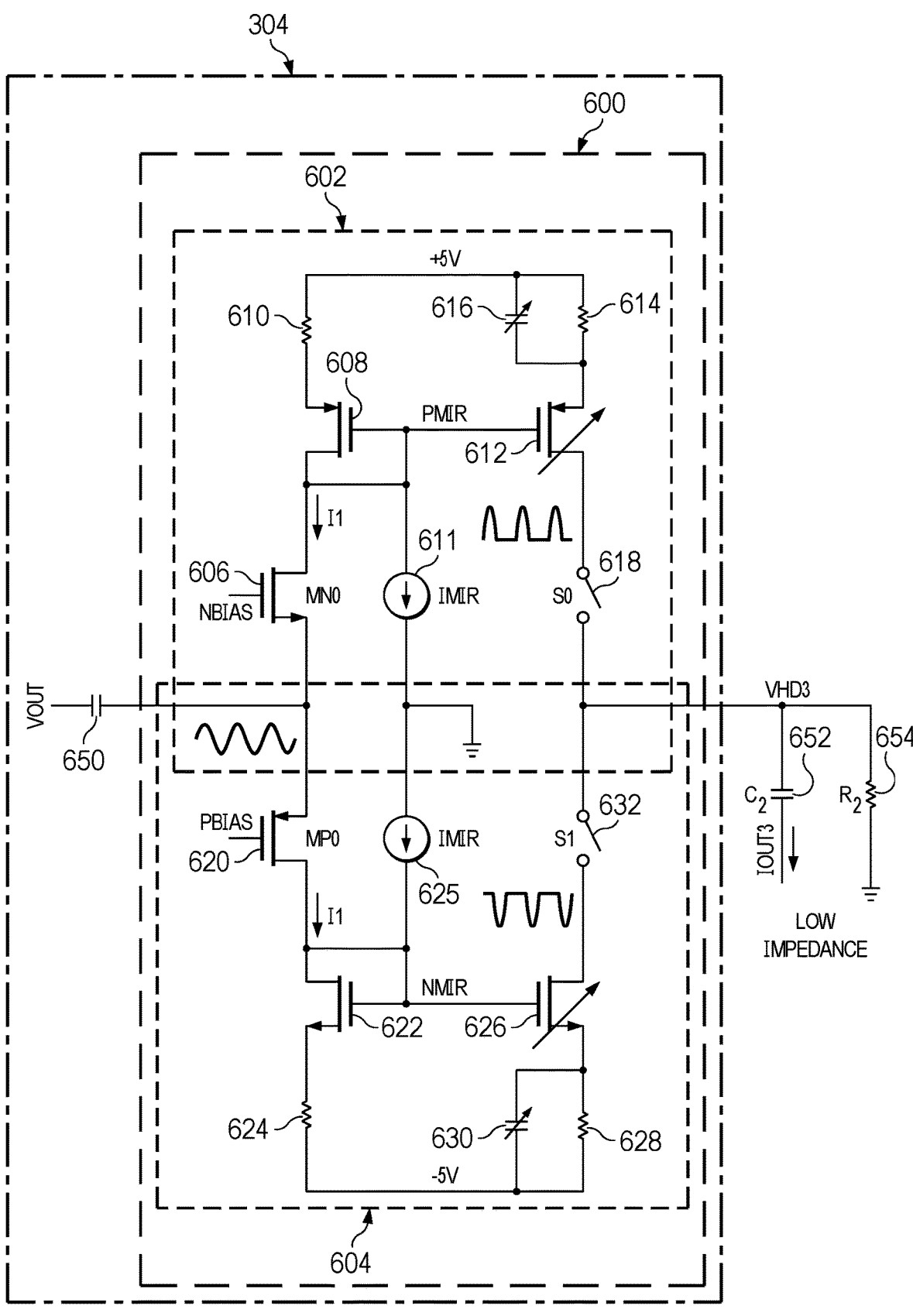
FIG. 6 is a diagram of an example circuit implementation of second error current correction circuitry of FIG. 3.

FIG. 6 is an example circuit implementation of the third error current correction circuitry 304 of FIG. 3. The third error current correction circuitry 304 includes an example current rectifier 600. The current rectifier 600 includes a positive current rectifier 602 and a negative current rectifier 604. The positive current rectifier 602 includes transistors 606, 608, 612, resistors 610, 614, a current source 611, a capacitor 616, and a switch 318. The negative current rectifier 604 includes transistors 620, 622, 626, resistors 624, 628, a current source 625, a capacitor 280, and a switch 632.

The third error current correction circuitry 304 further includes the capacitor 650. FIG. 6 further includes a capacitor 652 and a resistor 654. The operation of the current rectifier 600 is same as the current rectifier 400 of FIG. 4. However, the input terminal and the output terminal of the current rectifier 600 of FIG. 6 are coupled to different components than the current rectifier 400 of FIG. 4. Accordingly, for the sake of brevity, because the components of the rectifier 600 corresponds both structurally and functionally to the components of the rectifier 400 of FIG. 4, but for the different input connection and different output connection, the structure and function of the components of the rectifier 600 will not further be described except for the differences to the rectifier 400 of FIG. 4. Further description of the components can be ascertained from the above FIG. 4.

The resistors 654 of FIG. 6 includes a first terminal and a second terminal. The first terminal of the resistor 654 is coupled to the second terminals of the switch 618 and the switch 632 and the first terminal of the capacitor 652. The second terminal of the resistor 654 is coupled to the common terminal.

The capacitors 650, 652 of FIG. 6 each include a first terminal and a second terminal. The first terminal of the capacitor 650 is coupled to the output terminal of the output stage 208, the first terminal of the resistor 212, and the transducer 104. The second terminal of the capacitor 650 is coupled to the second current terminals of the transistors 606, 620. The first terminal of the capacitor 652 is coupled to the second terminals of the switches 618, 632 and the first terminal of the resistor 654. The second terminal of the capacitor 652 can be (e.g., depending on the implementation of the NLC circuitry 216 of FIG. 3) coupled to the output terminals(s) of the second current first and second error current correction circuitries 300, 302, the current correction combining circuitry 306, or the input terminal of the current buffer 308.

Like the capacitor 401 of FIG. 4, the capacitor 650 of FIG. 6 is a sensing capacitor. The current through the capacitor 650 is represented by SCV (e.g., the complex frequency of the Laplace transform time the capacitance of the capacitor 650). The sensed current is applied to the current rectifier 600. Because the rectifier 600 rectifies the input current, the rectifier 600 pumps a rectified current (e.g., [SCV]) into the resistor 654 to generate output voltage (VHD3) of the rectifier 600, shown in the below Equation 2.

$$VHD3 = K * |SC * Vout| * \left( \frac{R_2}{1 + SR_2 C_2} \right) \quad \text{(Equation 2)}$$

The capacitor 652 obtains the received output voltage to generate the ST*|SCV| error current (Iout3), where the pole generated by the capacitor 562 is cancelled based on the introduce zero in the |SCV| current generated by the capacitor 650 and the rectifier 600. The output error mitigation current corresponds to the below Equation 3.

$$Iout3 \sim K * SR_2 C_2 * |SC * Vout| \quad \text{(Equation 3)}$$

In some examples, magnitude profiles vary with swing rather than linearly proportional. In such examples, the resistor 654 can be replaced with a diode connected transistor to create a reducing nonlinearity with respect to swing.

As described above, the ST*|SCV| current can be used to mitigate ST*|SCV| nonlinear error. For example, during manufacturing the ST*|SCV| nonlinear error can be determined. Accordingly, one or more of the resistances of the resistors 614, 628, 654, the capacitance of the capacitors

616, 630, 650, 652, the size of the transistors 612, 626, or the operation of the switches 618, 632 can be selected to generate an ST*|SCV| error mitigation signal that is fed back into the HV driver 204 to mitigate the determined ST*|SCV| error.

Figure 7:
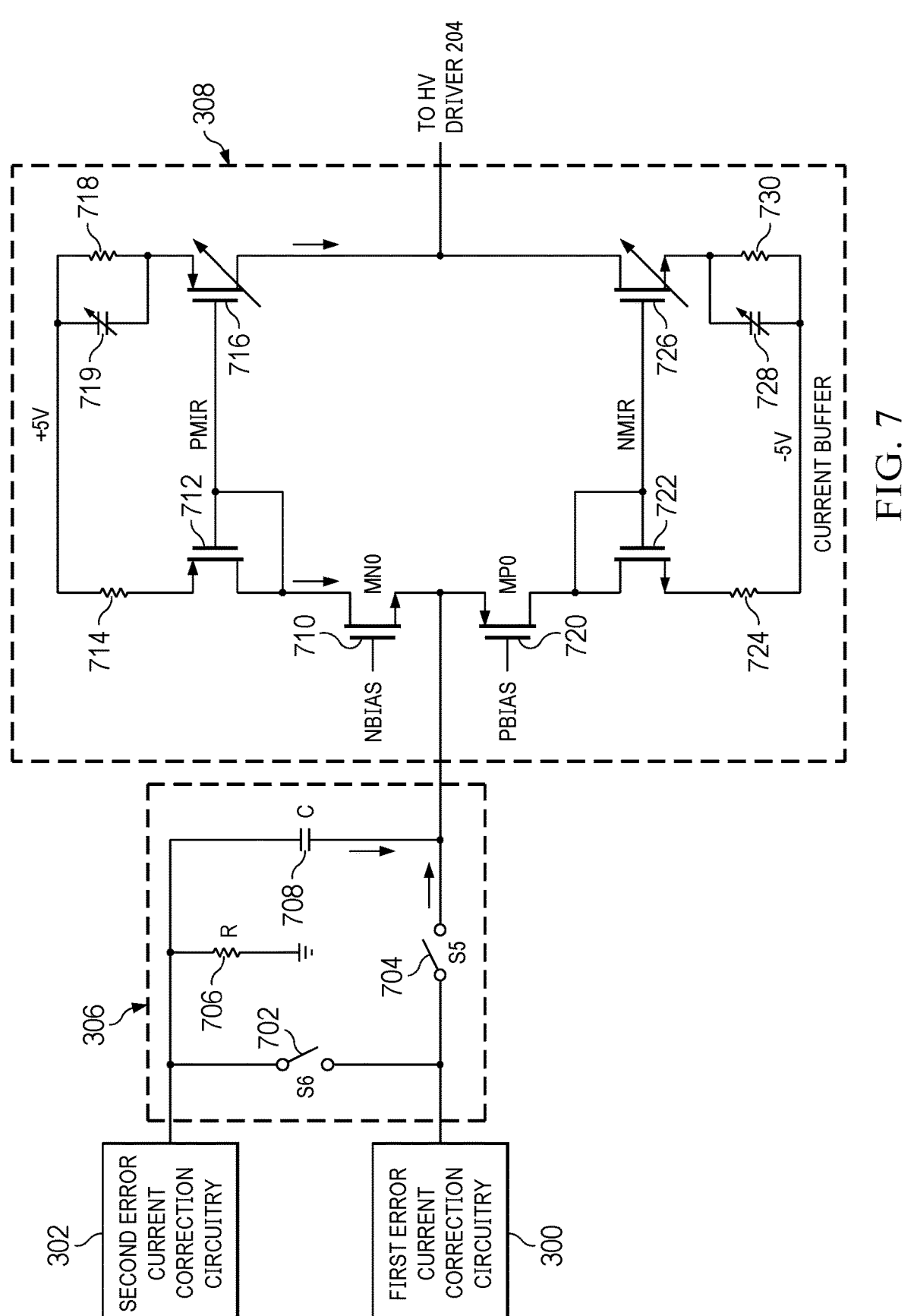
FIG. 7 is a diagram of an example circuit implementation of current correction combining circuitry and a current buffer of FIG. 3.

FIG. 7 illustrates an example circuit implementation of the current correction combining circuitry 306 of FIG. 3 and an example circuit implementation of the current buffer 308 of FIG. 3 in conjunction with the first error current correction circuitry 300 and the second current correction circuitry 302. The current correction combining circuitry 306 includes example switches 702, 704, an example resistor 706, and an example capacitor 708. The current buffer 308 includes example transistors 710, 716, 720, 722, 726, example resistors 714, 718, 724, 730, and example capacitors 719, 728.

The current combining circuitry 306 of FIG. 3 combines the outputs of the first error current correction circuitry 300 and the second error current correction circuitry 302. The current combining circuitry 306 includes three terminals. The first terminal of the current combining circuitry 306 is coupled to the first error current correction circuitry 300. The second terminal of the current combining circuitry 306 is coupled to the second error current correction circuitry 302. The third terminal of the current combining circuitry 306 is coupled to an input terminal of the current buffer 308. The resistor 706 and the capacitor 708 correspond to the resistor 554 and the capacitor 552 of FIG. 5 or the resistor 654 and the capacitor 652 of FIG. 6. The switches 702 each include a first terminal and a second terminal. The first terminal of the switch 702 is coupled to the second terminals of the switches 518, 532 of FIG. 5, the first terminal of the resistor 706, and the first terminal of the capacitor 708. The second terminal of the switch 702 is coupled to the second terminals of the switches 418, 432 of FIG. 4 and the first terminal of the switch 704. The first terminal of the switch 704 is coupled to the second terminals of the switches 418, 432 of FIG. 4 and the second terminal of the switch 702. The second terminal of the switch 704 is coupled to the second terminal of the capacitor 708 and the input terminal of the current buffer 308. The switches 702, 704 may be transistors (e.g., PMOS transistors, NMOS transistors, etc.).

The resistor 706 includes a first terminal and a second terminal. The first terminal of the resistor 706 is coupled to the second terminals of the switches 518, 532 of FIG. 5, the first terminal of the switch 702, and the first terminal of the capacitor 708. The second terminal of the resistor 706 is coupled to the common terminal (e.g., ground). The capacitor 708 includes a first terminal and a second terminal. The first terminal of the capacitor 708 is coupled to the second terminals of the switches 518, 532 of FIG. 5, the first terminal of the switch 702, and the first terminal of the resistor 706. The second terminal of the capacitor 708 is coupled to the second terminal of the switch 704 and the input terminal of the current buffer 308.

Because the difference the first error current correction circuitry 300 and the third error current correction circuitry 304 is the output circuitry, the output of the first error current correction circuitry 300 can be input into the resistor 706 and capacitor 708 to generate the output of the third error current correction circuitry 304 without including the circuitry of the third error current correction circuitry 304. Accordingly, the current combining circuitry 306 facilitates different combinations of error current correction without implementing all three current correction circuitries, thereby reducing area and resources. For example, if the switch 702 is off or disabled (e.g., creating an open circuit) and the switch 704 is enabled is on or enabled (e.g., creating a short circuit), the output of the second error current circuitry 302 is applied to the resistor 706 and the capacitor 708 to generate the SC|V| output current flowing from the capacitor 708 toward the current buffer 308. Also, the output of the first error current correction circuitry 300 (e.g., |SCV| output current) flows from the output of the first error current correction circuitry 300 toward the current buffer 308. Because the output of the first error current correction circuitry 300 is coupled to the output of the capacitor 708, the SC|V| output signal is combined with the |SCV| output signal. Thus, output signal of the current combining circuitry 306 is a sum of the |SCV| output current and the SC|V| output current. The output of the current combining circuitry 306 (e.g., |SCV|+SC|V|) is used to mitigate both |SCV| and SC|V| nonlinear error.

If the switch 702 is on or enabled and the switch 704 is off or disabled, the output of the first error current correction circuitry 300 is added to the output of the second current correction circuitry 302 to generate a summed output current (e.g., |SCV|+|V|). The summed output current is applied to the resistor 706 and capacitor 708 to generate an ST*|SCV|+SC|V| output current flowing from the capacitor 708 toward the current buffer 308. The ST*|SCV|+SC|V| output current is used to mitigate both SC|V| error and ST*|SCV| error.

If both the switches 702, 704 are disabled, then the first error current correction circuitry 300 is decoupled from the current buffer 308. Thus, the output of the current combining circuitry 306 will correspond to the SC|V| output signal to mitigate SC|V| error. The control of the switches 702, 704 can be based on the measured nonlinearity of the transmitter circuitry 102 during manufacturing. For example, if, during manufacturing, SC|V| and ST*|SCV| error is identified, the manufacturer can enable the switch 702 and disable the switch 704 and adjust the structure (e.g., gain and switches) of the first and second error current correction circuitries 300, 302 to generate an output signal that mitigates the SC|V| and ST*|SCV| error.

The transistor 710 includes a control terminal (e.g., a gate terminal), a first current terminal (e.g., a drain terminal), and a second current terminal (e.g., a source terminal). The control terminal of the transistor 710 is coupled to a bias current source. The bias current source provides low quiescent current (e.g., less than 1 microamperes (uA)) to bias the transistor 710. The first current terminal of the transistor 710 is coupled to the second current terminal of the transistor 712, and the control terminals of the transistors 712, 716. The second current terminal of the transistor 710 is coupled to the second terminal of the capacitor 401 and the first current terminal of the transistor 720. The transistor 710 is an n-channel metal oxide semiconductor field effect (NMOS or N-MOSFET) transistor. However, the transistor 710 may be a different type of transistor. The transistor 710 is biased based on a low quiescent current (e.g., less than 1 microamperes (uA)) provided by a bias current source.

The transistors 712, 716 of FIG. 7 each include a control terminal (e.g., a gate terminal), a first current terminal (e.g., a source terminal), and a second current terminal (e.g., a drain terminal). The control terminal of the transistor 712 is coupled to the control terminal of the transistor 716, the second current terminal of the transistor 712, and the first current terminal of the transistor 710. The first current terminal of the transistor 712 is coupled to the second terminal of the resistor 714. The second current terminal of the transistor 712 is coupled to the control terminals of the transistors 712, 716, and the first current terminal of the transistor 710. The control terminal of the transistor 716 coupled to the control terminal of the transistor 712, the second current terminal of the transistor 712, and the first current terminal of the transistor 710. The first current terminal of the transistor 716 is coupled to the second terminal of the capacitor 719 and the second terminal of the resistor 718. The second terminal of the transistor 716 coupled to the second terminal of the transistor 726 and the first terminal of the HV driver 204. The transistors 712, 716 are p-channel MOSFETs (e.g., PMOS transistors). However, the transistors 712, 716 can be any type of transistor. The transistors 712, 716 are structured to operate as a current mirror. Accordingly, the current flowing from the second terminal of the transistor 716 to HV driver 204 is proportional (e.g., with the same or a different gain) to the current flowing from the second current terminal of the transistor 712 to the first current terminal of the transistor 710. Accordingly, the output current of the current rectifier 400 corresponds to the positive rectified current based on the current through the capacitor 401. The amount of gain of the current mirror corresponding to transistors 712, 716 is based on the capacitance of the capacitor 719 and the size (e.g., channel width and length) of the transistor 716. The amount of capacitance or size of the transistor 716 can be selected to adjust the gain and phase of the current buffer 308.

The resistors 714, 718 and the capacitor 719 each have a first terminal and a second terminal. The first terminal of the resistor 714 is coupled to a positive supply terminal (e.g., +5 V). The second terminal of the resistor 714 is coupled to the first current source of the transistor 712. The first terminal of the resistor 718 is coupled to the positive supply terminal. The second terminal of the resistor 714 is coupled to the first current terminal of the transistor 716 and the second terminal of the capacitor 719. The first current terminal of the capacitor 719 is coupled to the positive supply terminal. The second current terminal of the capacitor 719 is coupled to the second terminal of the resistor 718 and the first current terminal of the transistor 716.

The transistor 720 includes a control terminal (e.g., a gate terminal), a first current terminal (e.g., a drain terminal), and a second current terminal (e.g., a source terminal). The control terminal of the transistor 720 is coupled to a bias current source. The bias current source provides current (e.g., 100 microamperes (uA)) to bias the transistor 720. The first current terminal of the transistor 720 is coupled to the second current terminal of the transistor 722, and the control terminals of the transistors 722, 726. The second current terminal of the transistor 720 is coupled to the second terminal of the capacitor 401 and the second current terminal of the transistor 710. The transistor 720 is a p-channel metal oxide semiconductor field effect (PMOS or P-MOSFET) transistor. However, the transistor 720 may be a different type of transistor. The transistor 720 is biased based on a current (e.g., 100 microamperes (uA)) provided by a bias current source.

The transistors 722, 726 of FIG. 7 each include a control terminal (e.g., a gate terminal), a first current terminal (e.g., a source terminal), and a second current terminal (e.g., a drain terminal). The control terminal of the transistor 722 is coupled to the control terminal of the transistor 726, the second current terminal of the transistor 722, and the first current terminal of the transistor 720. The first current terminal of the transistor 722 is coupled to the second terminal of the resistor 724. The second current terminal of the transistor 722 is coupled to the control terminals of the transistors 722, 726, and the first current terminal of the transistor 720. The control terminal of the transistor 726 coupled to the control terminal of the transistor 722, the second current terminal of the transistor 722, and the first current terminal of the transistor 720. The first current terminal of the transistor 726 is coupled to the second terminal of the capacitor 728 and the second terminal of the resistor 730. The second terminal of the transistor 726 coupled to the second terminal of the transistor 716 and the first terminal of the HV driver 204. The transistors 722, 726 are n-channel MOSFETs (e.g., NMOS transistors). However, the transistors 722, 726 can be any type of transistor. The transistors 722, 726 are structured to operate as a current mirror. Accordingly, the current flowing from the second terminal of the transistor 726 to the HV driver 204 is proportional (e.g., with the same or a different gain) to the current flowing from the second current terminal of the transistor 722 to the first current terminal of the transistor 720. Accordingly, the current flowing from the second current terminal of the transistor 726 toward the HV driver 204 corresponds to the negative rectified current of the output of the current combining circuitry 306. The amount of gain and phase of the current mirror corresponding to transistors 722, 726 is based on the capacitance of the capacitor 728 and the size (e.g., channel width and length) of the transistor 726. Because the second current terminal of the transistor 716 is coupled to the second current terminal of the transistor 726, the negative rectified current from second current terminal of the transistor 726 is added to the positive rectified current from the first current terminal of the transistor 716 to generate an output signal that is proportional to (e.g., the same as or with a different gain as) the output current signal from the current combining circuitry 306.

The resistors 724, 730 and the capacitor 728 each have a first terminal and a second terminal. The first terminal of the resistor 724 is coupled to a negative supply terminal (e.g., −5 V). The second terminal of the resistor 724 is coupled to the first current source of the transistor 722. The first terminal of the resistor 730 is coupled to the negative supply terminal. The second terminal of the resistor 724 is coupled to the first current terminal of the transistor 726 and the second terminal of the capacitor 728. The first current terminal of the capacitor 728 is coupled to the negative supply terminal. The second current terminal of the capacitor 728 is coupled to the second terminal of the resistor 730 and the first current terminal of the transistor 726.

Figure 8:
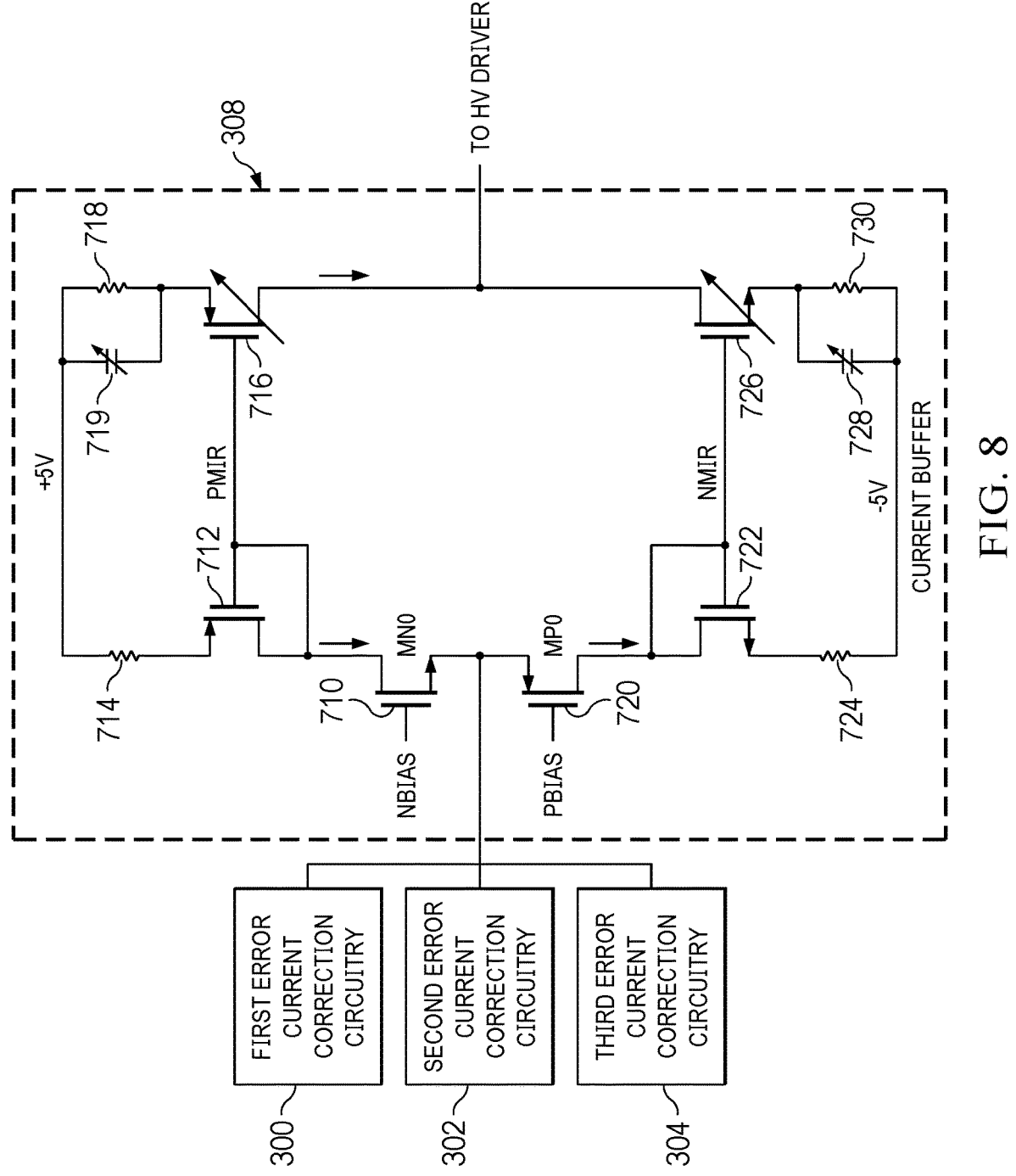
FIG. 8 is a diagram of an alternative example circuit implementation of non-linear correction circuitry of FIG. 2.

FIG. 8 illustrates an example circuit implementation of the current buffer 308 of FIG. 3 in conjunction with the first error current correction circuitry 300, the second current correction circuitry 302, and the third current correction circuitry 304 of FIG. 3. The current buffer 308 includes example transistors 710, 716, 720, 722, 726, example resistors 714, 718, 724, 730, and example capacitors 719, 728 of FIG. 7. The operation of the current buffer 308 of FIG. 8 is same as the current buffer 308 of FIG. 7. However, the input terminal of the current buffer 308 of FIG. 8 is coupled to different components than the current buffer 308 of FIG. 7. Accordingly, for the sake of brevity, because the components of the current buffer 308 of FIG. 8 corresponds both structurally and functionally to the components of the current buffer 308 of FIG. 7, but for the different input connection, the structure and function of the components of the current buffer 308 of FIG. 7 will not further be described except for the differences to the current buffer 308 of FIG. 7. Further description of the components can be ascertained from the above description in FIG. 7.

In the example of FIG. 8, the output terminal of the first error circuitry 300 (e.g., the second terminals of the switches 418, 432) is coupled to the output terminals of the second error correction circuitry 302 (e.g., the second terminal of the capacitor 552), the output of the third error current correction circuitry 304 (e.g., the second terminal of the capacitor 652) and the input terminal of the current buffer 308. The output terminal of the second error circuitry 302 is coupled to the output terminal of the first error current correction circuitry 300, the output terminal of the third error current correction circuitry 304, and the input terminal of the current buffer 308. The output terminal of the third error correction circuitry 304 is coupled to the output terminal of the first error current correction circuitry 300, the output terminal of the second error current correction circuitry 302, and the input terminal of the current buffer 308.

In the example of FIG. 8, the current combining circuitry 306 is not included. Rather, the output current signals from the first, second, and third current correction circuitries 300, 302, 304 are all combined (e.g., summed) and applied to the input terminal of the current buffer 308. Accordingly, the input current signal to the current buffer 308 corresponds to the combination of signals to mitigate |SCV| nonlinearity, SC|V| nonlinearity, and ST*|SCV| nonlinearity.

One or more example manners of implementing the transmitter circuitry 102 of FIG. 1 is illustrated in FIGS. 2-8. However, one or more of the elements, processes or devices illustrated in FIG. 1 may be combined, divided, re-arranged, omitted, eliminated or implemented in any other way.

Further, one or more of the input stage 202, the HV driver 204, the output stage 208, the NLC circuitry 216, 218 may be implemented by one or more of hardware, software, firmware or any combination of hardware, software or firmware. As a result, for example, any one or more of the input stage 202, the HV driver 204, the output stage 208, the NLC circuitry 216, 218 could be implemented by one or more analog or digital circuit(s), logic circuits, programmable processor(s), programmable controller(s), graphics processing unit(s) (GPU(s)), digital signal processor(s) (DSP(s)), application specific integrated circuit(s) (ASIC(s)), programmable logic device(s) (PLD(s)) or field programmable logic device(s) (FPLD(s)).

When reading any of the apparatus or system claims of this patent to cover a purely software or firmware implementation, at least one of the input stage 202, the HV driver 204, the output stage 208, the NLC circuitry 216, 218 is/are hereby expressly defined to include a non-transitory computer readable storage device or storage disk such as a memory, a digital versatile disk (DVD), a compact disk (CD), a Blu-ray disk, etc., including the software or firmware. Further still, one or more of one or more of the input stage 202, the HV driver 204, the output stage 208, the NLC circuitry 216, 218 may include one or more elements, processes or devices in addition to, or instead of, those illustrated in FIG. 2, or may include more than one of any or all of the illustrated elements, processes, and devices. As used herein, the phrase "in communication," including variations thereof, encompasses direct communication or indirect communication through one or more intermediary components, and does not require direct physical (e.g., wired) communication or constant communication, but rather also includes selective communication at one or more of periodic intervals, scheduled intervals, aperiodic intervals, or one-time events.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

Descriptors "first," "second," "third," etc. are used herein to identify multiple elements or components which may be referred to separately. Unless otherwise specified or known based on their context of use, such descriptors do not impute any meaning of priority, physical order, or arrangement in a list, or ordering in time but are merely used as labels for referring to multiple elements or components separately for ease of understanding the described examples. In some examples, the descriptor "first" may be used to refer to an element in the detailed description, while the same element may be referred to in a claim with a different descriptor such as "second" or "third." In such instances, such descriptors are used merely for ease of referencing multiple elements or components.

In the description and in the claims, the terms "including" and "having," and variants thereof are to be inclusive in a manner similar to the term "comprising" unless otherwise noted. Unless otherwise stated, "about," "approximately," or "substantially" preceding a value means+/−10 percent of the stated value. In another example, "about," "approximately," or "substantially" preceding a value means+/−5 percent of the stated value. IN another example, "about," "approximately," or "substantially" preceding a value means+/−1 percent of the stated value.

The terms "couple," "coupled," "couples," and variants thereof, as used herein, may cover connections, communications, or signal paths that enable a functional relationship consistent with this description. For example, if device A generates a signal to control device B to perform an action, if a first example device A is coupled to device B, or if a second example device A is coupled to device B through intervening component C if intervening component C does not substantially alter the functional relationship between device A and device B, such that device B is controlled by device A via the control signal generated by device A. Moreover, the terms "couple," "coupled", "couples", or variants thereof, includes an indirect or direct electrical or mechanical connection.

A device that is "configured to" perform a task or function may be configured (e.g., at least one of programmed or hardwired) at a time of manufacturing by a manufacturer to perform the function or may be configurable (or re-configurable) by a user after manufacturing to perform the function or other additional or alternative functions. The configuring may be through at least one of firmware or software programming of the device, through a construction or layout of hardware components and interconnections of the device, or a combination thereof.

Although not all separately labeled in the FIG. 2, components or elements of systems and circuits illustrated therein have one or more conductors or terminus that allow signals into or out of the components or elements. The conductors or terminus (or parts thereof) may be referred to herein as pins, pads, terminals (including input terminals, output terminals, reference terminals, and ground terminals, for instance), inputs, outputs, nodes, and interconnects.

As used herein, a "terminal" of a component, device, system, circuit, integrated circuit, or other electronic or semiconductor component, generally refers to a conductor such as a wire, trace, pin, pad, or other connector or interconnect that enables the component, device, system, etc., to electrically or mechanically connect to another component, device, system, etc. A terminal may be used, for instance, to receive or provide analog or digital electrical signals (or simply signals) or to electrically connect to a common or ground reference. Accordingly, an input terminal or input is used to receive a signal from another component, device, system, etc. An output terminal or output is used to provide a signal to another component, device, system, etc. Other terminals may be used to connect to a common, ground, or voltage reference, e.g., a reference terminal or ground terminal. A terminal of an IC or a PCB may also be referred to as a pin (a longitudinal conductor) or a pad (a planar conductor). A node refers to a point of connection or interconnection of two or more terminals. An example number of terminals and nodes may be shown. However, depending on particular circuitry or system topology, there may be more or fewer terminals and nodes. However, in some instances, "terminal," "node," "interconnect," "pad," and "pin" may be used interchangeably.

The term "or" as used, for example, in a form such as A, B, or C refers to any combination or subset of A, B, C such as (1) A alone, (2) B alone, (3) C alone, (4) A with B, (5) A with C, (6) B with C, or (7) A with B and with C.

Example methods, apparatus, systems, and articles of manufacture to correct non-linearity in transmitters are described herein. Further examples and combinations thereof include the following: Example 1 includes an apparatus comprising a first transistor having a control terminal, a first current terminal, and a second current terminal, the control terminal of the first transistor coupled to the second current terminal of the first transistor, the first current terminal of the first transistor coupled to a supply terminal via a first resistor, a second transistor having a control terminal, a first current terminal, and a second current terminal, the control terminal of the second transistor coupled to the control terminal of the first transistor and the second current terminal of the first transistor, the first current terminal of the second transistor coupled to the supply terminal via a second resistor and a capacitor, a current source having a first terminal and a second terminal, the first terminal of the current source coupled to the control terminals of the first and second transistors, and the second current terminal of the first transistor, the second terminal of the current source coupled to a common terminal, and a switch having a first terminal and a second terminal, the first terminal of the switch coupled to the second current terminal of the second transistor.

Example 2 includes the apparatus of example 1, wherein the capacitor and the first transistor coupled in parallel.

Example 3 includes the apparatus of example 1, further including a third transistor having a control terminal, a first current terminal, and a second current terminal, the first current terminal of the third transistor coupled to the second current terminal and the control terminal of the first transistor, the first terminal of the current source, and the control terminal of the second transistor.

Example 4 includes the apparatus of example 3, wherein the capacitor is a first capacitor, further including a second capacitor having a first terminal and a second terminal, the first terminal of the second capacitor coupled to an output of a buffer, the second terminal of the second capacitor coupled to the second current terminal of the third transistor.

Example 5 includes the apparatus of example 4, further including a third resistor having a first terminal and a second terminal, the first terminal of the third resistor coupled to the first terminal of the second capacitor and the output of the buffer, the second terminal of the third resistor coupled to the second terminal of the second capacitor and the second current terminal of the third transistor.

Example 6 includes the apparatus of example 5, further including a fourth resistor having a first terminal and a second terminal, the first terminal of the fourth resistor coupled to the second terminal of the switch, the second terminal of the fourth resistor coupled to the common terminal, and a third capacitor having a first terminal and a second terminal, the first terminal of the third capacitor coupled to the first terminal of the fourth resistor and the second terminal of the switch, the second terminal of the third transistor coupled to a current buffer.

Example 7 includes the apparatus of example 4, further including a third resistor having a first terminal and a second terminal, the first terminal of the third resistor coupled to the second terminal of the switch, the second terminal of the third resistor coupled to the common terminal, and a third capacitor, the first terminal of the third capacitor coupled to the first terminal of the third resistor and the second terminal of the switch, the second terminal of the third capacitor coupled to a current buffer.

Example 8 includes the apparatus of example 3, wherein the current source is a first current source, the switch is a first switch, and the capacitor is a first capacitor, further including a fourth transistor having a control terminal, a first current terminal, and a second current terminal, the control terminal of the fourth transistor coupled to the first current terminal of the fourth transistor, the second current terminal of the fourth transistor coupled to a negative supply terminal via a third resistor, a fifth transistor having a control terminal, a first current terminal, and a second current terminal, the control terminal of the fifth transistor coupled to the control terminal of the fourth transistor and the first current terminal of the fourth transistor, the second current terminal of the fifth transistor coupled to the negative supply terminal via a fourth resistor and a second capacitor, a second current source having a first terminal and a second terminal, the first terminal of the second current source coupled to the common terminal and the second terminal of the first current source, the second terminal of the second current source coupled to the control terminals of the first and fifth transistors, and the second current terminal of the fourth transistor, and a second switch having a first terminal and a second terminal, the first terminal of the second switch coupled to the second terminal of the first switch, the second terminal of the second switch coupled to the first current terminal of the fifth transistor.

Example 9 includes an apparatus comprising first error current correction circuitry having a first terminal and a second terminal, second error current correction circuitry having a first terminal and a second terminal, a first switch having a first terminal and a second terminal, the first terminal of the first switch coupled to the second terminal of the first error current correction circuitry, the second terminal of the first switch coupled to the second terminal of the second error current correction circuitry, a second switch having a first terminal and a second terminal, the first terminal of the second switch is coupled to the second terminal of the first switch and the second terminal of the second error current correction circuitry, the second terminal of the second switch coupled to a current buffer, a resistor having a first terminal and a second terminal, the first terminal of the resistor coupled to the second terminal of the first error current correction circuitry and the first terminal of the first switch, the second terminal of the resistor coupled to a common terminal, and a capacitor having a first terminal and a second terminal, the first terminal of the capacitor coupled to the second terminal of the first error current correction circuitry, the first terminal of the first switch, and the first terminal of the resistor, the second terminal of the capacitor coupled to the second terminal of the second switch and the current buffer.

Example 10 includes the apparatus of example 9, wherein the first error current correction circuitry includes positive half rectifier circuitry having an input terminal and an output terminal, the output terminal of the positive half rectifier circuitry being the second terminal of the first error current correction circuitry, and negative half rectifier circuitry having an input terminal and an output terminal, the input terminal of the negative half rectifier circuitry being the input terminal of the positive half rectifier circuitry, the output terminal of the negative half rectifier circuitry being the output terminal of the positive half rectifier circuitry.

Example 11 includes the apparatus of example 10, wherein the capacitor is a first capacitor, further including a second capacitor having a first terminal and a second terminal, the first terminal of the second capacitor coupled to an output buffer, the second terminal of the second capacitor coupled to the input terminal of the positive half rectifier circuitry and the input terminal of the negative half rectifier circuitry.

Example 12 includes the apparatus of example 9, wherein the second error current correction circuitry includes positive half rectifier circuitry having an input terminal and an output terminal, the output terminal of the positive half rectifier circuitry being the second terminal of the second error current correction circuitry, and negative half rectifier circuitry having an input terminal and an output terminal, the input terminal of the negative half rectifier circuitry being the input terminal of the positive half rectifier circuitry, the output terminal of the negative half rectifier circuitry being the output terminal of the positive half rectifier circuitry.

Example 13 includes the apparatus of example 10, wherein the resistor is a first resistor and the capacitor is a first capacitor, further including a second capacitor having a first terminal and a second terminal, the first terminal of the second capacitor coupled to an output buffer, the second terminal of the second capacitor coupled to the input terminal of the positive half rectifier circuitry and the input terminal of the negative half rectifier circuitry, and a second resistor having a first terminal and a second terminal, the first terminal of the second resistor coupled to the first terminal of the second capacitor and the output buffer, the second terminal of the second resistor coupled to the second terminal of the second capacitor and the input terminal of the positive half rectifier circuitry and the input terminal of the negative half rectifier circuitry.

Example 14 includes the apparatus of example 9, wherein the resistor is a first resistor and the capacitor is a first capacitor, the first error current correction circuitry including a first transistor having a control terminal, a first current terminal, and a second current terminal, the control terminal of the first transistor coupled to the second current terminal of the first transistor, the first current terminal of the first transistor coupled to a supply terminal via a second resistor, a second transistor having a control terminal, a first current terminal, and a second current terminal, the control terminal of the second transistor coupled to the control terminal of the first transistor and the second current terminal of the first transistor, the first current terminal of the second transistor coupled to the supply terminal via a third resistor and a second capacitor, a current source having a first terminal and a second terminal, the first terminal of the current source coupled to the control terminals of the first and second transistors, and the second current terminal of the first transistor, the second terminal of the current source coupled to a common terminal, and a switch having a first terminal and a second terminal, the first terminal of the switch coupled to the second current terminal of the second transistor, the second terminal of the switch being the second terminal of the first error current correction circuitry.

Example 15 includes a transmitter comprising an input stage having a first input terminal, a second input terminal and an output terminal, a driver having an input terminal and an output terminal, the input terminal of the driver coupled to the output terminal of the input stage, an output buffer having an input terminal and an output terminal, the input terminal of the output buffer coupled to the output terminal of the driver, the output terminal of the output terminal coupled to the first input terminal of the input stage via a resistor, and non-linear correction circuitry having an input terminal and an output terminal, the input terminal of the non-linear correction circuitry coupled to the output terminal of the output buffer and the first input terminal of the input stage via the resistor, the output terminal of the non-linear correction circuitry coupled to the output terminal of the input stage and the input terminal of the driver.

Example 16 includes the transmitter of example 15, further including a signal generator having a first terminal and a second terminal, the first terminal coupled to the second terminal of the input stage, the second terminal of the signal generator coupled to a common terminal.

Example 17 includes the transmitter of example 15, wherein the resistor is a first resistor having a first terminal and a second terminal, further including a second resistor having a first terminal and a second terminal, the first terminal of the second resistor coupled to the second terminal of the first resistor and the first input terminal of the input stage, the second terminal of the second resistor coupled to a common terminal.

Example 18 includes the transmitter of example 15, wherein the non-linear correction circuitry is first non-linear correction circuitry, further including second non-linear correction circuitry including an input terminal and an output terminal, the input terminal of the second non-linear correction circuitry coupled to the second input terminal of the input stage, the output terminal of the second non-linear correction circuitry coupled to the output terminal of the input stage, the input terminal of the driver, and the output terminal of the first non-linear correction circuitry.

Example 19 includes the transmitter of example 15, wherein the output terminal of the output buffer is structured to be coupled to a transducer.

Example 20 includes the transmitter of example 15, wherein the non-linear correction circuitry includes a capacitor including a first terminal and a second terminal, the first terminal of the capacitor being the first terminal of the non-linear correction circuitry, positive half rectifier circuitry having an input terminal and an output terminal, the input terminal of the positive half rectifier circuitry coupled to the second terminal of the capacitor, the output terminal of the positive half rectifier circuitry coupled to the input terminal of the driver via a current buffer, and negative half rectifier circuitry having an input terminal and an output terminal, the input terminal of the negative half rectifier circuitry coupled to the second terminal of the capacitor and the first terminal of the negative half rectifier circuitry, the output terminal of the negative half rectifier circuitry coupled to the input terminal of the driver via the current buffer and the output terminal of the positive half rectifier circuitry.

Modifications are possible in the described examples, and other examples are possible, within the scope of the claims.

What is claimed is:

1. An apparatus comprising:
a first capacitor having a first terminal and a second terminal;
a first transistor having a control terminal, a first current terminal, and a second current terminal, the control terminal of the first transistor coupled to the second current terminal of the first transistor, the second current terminal of the first transistor coupled to the second terminal of the first capacitor;
a first resistor having a first terminal and a second terminal, the first terminal of the first resistor coupled to a supply terminal and a second terminal of the first resistor coupled to the first current terminal of the first transistor;
a second transistor having a control terminal, a first current terminal, and a second current terminal, the control terminal of the second transistor coupled to the control terminal of the first transistor and the second current terminal of the first transistor;
a second capacitor having a first terminal and a second terminal, the first terminal of the second capacitor coupled to the supply terminal, the second terminal of the second capacitor coupled to the first current terminal of the second transistor;
a second resistor having a first terminal and a second terminal, the first terminal of the second resistor coupled to the supply terminal, the second terminal of the second resistor coupled to the first current terminal of the second transistor and the second terminal of the second capacitor;
a current source circuit having a first terminal and a second terminal, the first terminal of the current source circuit coupled to the control terminals of the first and second transistors, and the second current terminal of the first transistor, the second terminal of the current source circuit coupled to a common terminal; and
a switch having a first terminal and a second terminal, the first terminal of the switch coupled to the second current terminal of the second transistor.

2. The apparatus of claim 1, wherein the second capacitor and the second resistor coupled in parallel.

3. The apparatus of claim 1, further including a third transistor having a control terminal, a first current terminal, and a second current terminal, the first current terminal of the third transistor coupled to the second current terminal and the control terminal of the first transistor, the first terminal of the current source circuit, and the control terminal of the second transistor.

4. The apparatus of claim 3, wherein the second terminal of the first capacitor is coupled to the second terminal of the first transistor via the third transistor.

5. The apparatus of claim 4, further including a third resistor having a first terminal and a second terminal, the first terminal of the third resistor coupled to the first terminal of the first capacitor, the second terminal of the third resistor coupled to the second terminal of the first capacitor and the second current terminal of the third transistor.

6. The apparatus of claim 5, further including:

a fourth resistor having a first terminal and a second terminal, the first terminal of the fourth resistor coupled to the second terminal of the switch, the second terminal of the fourth resistor coupled to the common terminal; and a third capacitor having a first terminal and a second terminal, the first terminal of the third capacitor coupled to the first terminal of the fourth resistor and the second terminal of the switch, the second terminal of the third transistor coupled to a current buffer.

7. The apparatus of claim 4, further including:

a third resistor having a first terminal and a second terminal, the first terminal of the third resistor coupled to the second terminal of the switch, the second terminal of the third resistor coupled to the common terminal; and a third capacitor, the first terminal of the third capacitor coupled to the first terminal of the third resistor and the second terminal of the switch, the second terminal of the third capacitor coupled to a current buffer.

8. The apparatus of claim 3, wherein the current source circuit is a first current source circuit and the switch is a first switch, further including:

a fourth transistor having a control terminal, a first current terminal, and a second current terminal, the control terminal of the fourth transistor coupled to the first current terminal of the fourth transistor, the second current terminal of the fourth transistor coupled to a negative supply terminal via a third resistor;

a fifth transistor having a control terminal, a first current terminal, and a second current terminal, the control terminal of the fifth transistor coupled to the control terminal of the fourth transistor and the first current terminal of the fourth transistor, the second current terminal of the fifth transistor coupled to the negative supply terminal via a fourth resistor and a third capacitor;

a second current source circuit having a first terminal and a second terminal, the first terminal of the second current source circuit coupled to the common terminal and the second terminal of the first current source circuit, the second terminal of the second current source circuit coupled to the control terminals of the first and fifth transistors, and the second current terminal of the fourth transistor; and a second switch having a first terminal and a second terminal, the first terminal of the second switch coupled to the second terminal of the first switch, the second terminal of the second switch coupled to the first current terminal of the fifth transistor.

9. An apparatus comprising:

a current buffer including a first terminal and a second terminal;

first error current correction circuitry having a first terminal and a second terminal;

second error current correction circuitry having a first terminal and a second terminal;

a first switch having a first terminal and a second terminal, the first terminal of the first switch coupled to the second terminal of the first error current correction circuitry, the second terminal of the first switch coupled to the second terminal of the second error current correction circuitry;

a second switch having a first terminal and a second terminal, the first terminal of the second switch is coupled to the second terminal of the first switch and the second terminal of the second error current correction circuitry, the second terminal of the second switch coupled to the first terminal of the current buffer;

a resistor having a first terminal and a second terminal, the first terminal of the resistor coupled to the second terminal of the first error current correction circuitry and the first terminal of the first switch, the second terminal of the resistor coupled to a common terminal; and a capacitor having a first terminal and a second terminal, the first terminal of the capacitor coupled to the second terminal of the first error current correction circuitry, the first terminal of the first switch, and the first terminal of the resistor, the second terminal of the capacitor coupled to the second terminal of the second switch and the first terminal of the current buffer.

10. The apparatus of claim 9, wherein the first error current correction circuitry includes:

positive half rectifier circuitry having an input terminal and an output terminal, the output terminal of the positive half rectifier circuitry being the second terminal of the first error current correction circuitry; and negative half rectifier circuitry having an input terminal and an output terminal, the input terminal of the negative half rectifier circuitry being the input terminal of the positive half rectifier circuitry, the output terminal of the negative half rectifier circuitry being the output terminal of the positive half rectifier circuitry.

11. The apparatus of claim 10, wherein the capacitor is a first capacitor, further including a second capacitor having a first terminal and a second terminal, the first terminal of the second capacitor coupled to an output buffer, the second terminal of the second capacitor coupled to the input terminal of the positive half rectifier circuitry and the input terminal of the negative half rectifier circuitry.

12. The apparatus of claim 9, wherein the second error current correction circuitry includes:

positive half rectifier circuitry having an input terminal and an output terminal, the output terminal of the positive half rectifier circuitry being the second terminal of the second error current correction circuitry; and negative half rectifier circuitry having an input terminal and an output terminal, the input terminal of the negative half rectifier circuitry being the input terminal of the positive half rectifier circuitry, the output terminal of the negative half rectifier circuitry being the output terminal of the positive half rectifier circuitry.

13. The apparatus of claim 10, wherein the resistor is a first resistor and the capacitor is a first capacitor, further including:

a second capacitor having a first terminal and a second terminal, the first terminal of the second capacitor coupled to an output buffer, the second terminal of the second capacitor coupled to the input terminal of the positive half rectifier circuitry and the input terminal of the negative half rectifier circuitry; and a second resistor having a first terminal and a second terminal, the first terminal of the second resistor coupled to the first terminal of the second capacitor and the output buffer, the second terminal of the second resistor coupled to the second terminal of the second capacitor and the input terminal of the positive half rectifier circuitry and the input terminal of the negative half rectifier circuitry.

14. The apparatus of claim 9, wherein the resistor is a first resistor and the capacitor is a first capacitor, the first error current correction circuitry including:

a first transistor having a control terminal, a first current terminal, and a second current terminal, the control terminal of the first transistor coupled to the second current terminal of the first transistor, the first current terminal of the first transistor coupled to a supply terminal via a second resistor;

a second transistor having a control terminal, a first current terminal, and a second current terminal, the control terminal of the second transistor coupled to the control terminal of the first transistor and the second current terminal of the first transistor, the first current terminal of the second transistor coupled to the supply terminal via a third resistor and a second capacitor;

a current source circuit having a first terminal and a second terminal, the first terminal of the current source circuit coupled to the control terminals of the first and second transistors, and the second current terminal of the first transistor, the second terminal of the current source circuit coupled to a common terminal; and a switch having a first terminal and a second terminal, the first terminal of the switch coupled to the second current terminal of the second transistor, the second terminal of the switch being the second terminal of the first error current correction circuitry.

15. A transmitter comprising:

an input stage having a first input terminal, a second input terminal and an output terminal, a driver having an input terminal and an output terminal, the input terminal of the driver coupled to the output terminal of the input stage;

an output buffer having an input terminal and an output terminal, the input terminal of the output buffer coupled to the output terminal of the driver, the output terminal of the output terminal coupled to the first input terminal of the input stage via a resistor; and non-linear correction circuitry having an input terminal and an output terminal, the input terminal of the non-linear correction circuitry coupled to the output terminal of the output buffer and the first input terminal of the input stage via the resistor, the output terminal of the non-linear correction circuitry coupled to the output terminal of the input stage and the input terminal of the driver.

16. The transmitter of claim 15, further including a signal generator having a first terminal and a second terminal, the first terminal coupled to the second terminal of the input stage, the second terminal of the signal generator coupled to a common terminal.

17. The transmitter of claim 15, wherein the resistor is a first resistor having a first terminal and a second terminal, further including a second resistor having a first terminal and a second terminal, the first terminal of the second resistor coupled to the second terminal of the first resistor and the first input terminal of the input stage, the second terminal of the second resistor coupled to a common terminal.

18. The transmitter of claim 15, wherein the non-linear correction circuitry is first non-linear correction circuitry, further including second non-linear correction circuitry including an input terminal and an output terminal, the input terminal of the second non-linear correction circuitry coupled to the second input terminal of the input stage, the output terminal of the second non-linear correction circuitry coupled to the output terminal of the input stage, the input terminal of the driver, and the output terminal of the first non-linear correction circuitry.

19. The transmitter of claim 15, wherein the output terminal of the output buffer is structured to be coupled to a transducer.

20. The transmitter of claim 15, wherein the non-linear correction circuitry includes:

a current buffer;

a capacitor including a first terminal and a second terminal, the first terminal of the capacitor being the first terminal of the non-linear correction circuitry;

positive half rectifier circuitry having an input terminal and an output terminal, the input terminal of the positive half rectifier circuitry coupled to the second terminal of the capacitor, the output terminal of the positive half rectifier circuitry coupled to the input terminal of the driver via the current buffer; and negative half rectifier circuitry having an input terminal and an output terminal, the input terminal of the negative half rectifier circuitry coupled to the second terminal of the capacitor and the first terminal of the negative half rectifier circuitry, the output terminal of the negative half rectifier circuitry coupled to the input terminal of the driver via the current buffer and the output terminal of the positive half rectifier circuitry.

\* \* \* \* \*